US006455678B1

(12) United States Patent
Yin et al.

(10) Patent No.: US 6,455,678 B1
(45) Date of Patent: Sep. 24, 2002

(54) HUMAN HEMATOPOIETIC STEM AND PROGENITOR CELL ANTIGEN

(75) Inventors: Amy H. Yin, San Jose; Sheri Miraglia, Palo Alto; Wayne G. Godfry, Atherton; David W. Buck, Santa Clara, all of CA (US)

(73) Assignee: AmCell Corporation, Burlingame, CA (US)

(*) Notice: Subject to any disclaimer, the term of this patent is extended or adjusted under 35 U.S.C. 154(b) by 0 days.

(21) Appl. No.: 08/842,382

(22) Filed: Apr. 23, 1997

Related U.S. Application Data

(63) Continuation-in-part of application No. 08/639,891, filed on Apr. 26, 1996.

(51) Int. Cl.$^7$ ................................................. C07K 1/00
(52) U.S. Cl. ........................ 530/395; 530/350; 530/806; 530/838
(58) Field of Search ............................... 530/350, 395, 530/806, 838

(56) References Cited

U.S. PATENT DOCUMENTS

| | | | |
|---|---|---|---|
| 4,452,773 A | | 6/1984 | Molday |
| 4,714,680 A | | 12/1987 | Civin |
| 5,061,620 A | | 10/1991 | Tsukamoto et al. |
| 5,248,599 A | * | 9/1993 | Sariyama et al. |
| 5,411,863 A | | 5/1995 | Miltenyi |
| 5,573,930 A | * | 11/1996 | Ladner et al. |

FOREIGN PATENT DOCUMENTS

EP     0 662 512     7/1995

OTHER PUBLICATIONS

Mikayama et al. Molecular Cloning & Functional Expression of a cDNA . . . P.N.A.S. (90) 10056–10060. 1993.*
Hardwick, A., et al., "Development of a Large–Scale Immunomagnetic Separation System for Harvesting CD34–Positive Cells From Bone Marrow," Advances in Bone Marrow Purging and Processing, pp. 583–589 (1992).
Oku, Naritoshi, et at., "Monitoring o fKinetics of CD34 Positive Cells By Immunomagnetic Beads During Peripheral Blood Stem Cell Harvest for Autotransplantation," Advances in Bone Marrow Purging and Processing, pp. 553–560 (1992).
Bigas, A., et al., "CD34 Positive Cell Selection By Immunomagnetic Techniques," Advances in Bone Marrow Purging and Processing, pp. 545–551 (1992).
Thomas, T.E., et al., "Purification of CD34 Positive Cells from Human Bone Marrow Using High Gradient Magnetic Separation," Advances in Bone Marrow Purging and Processing, pp. 537–544 (1992).

Grimsley, P.G., et al., "Rapid Positive Selection of CD34 + Cells Using Magnetic Microspheres Coated with Monoclonal Antibody QBEND/10 Linked via a Cleavable Disulphide Bond," Leukemia, vol. 7, No. 6:898–908 (1993).
Miltenyi, S., et al., "High Gradient Magnetic Cell Separation with MACS," pp. 231–238 (1990).
McNiece, I.K., "Detection of a Human CFC with a High Proliferative Potential," Blood, vol. 74, (No. 2) :609–612 (Aug. 1, 1989).
Gordon, M.Y., et al., "Characterisation of Stroma–Dependent Blast Colony–Forming Cells in Human Marrow," Journal of Cellular Physiology, pp. 150–156 (1987).
Spangrude, G.J., et al., "Resting and activated subsets of mouse multipotent hematopoietic stem cells," pp. 7433–7439 (Jun. 18, 1990).
Brandt, J., et al., "Cytokine–dependent Long–Term Culture of Highly Enriched Precursors of Hematopoietic Progenitor Cells from Human Bone Marrow," The American Society for Clinical Investigation, Inc., pp. 932–941 (Sep. 1990).
To, L.B., et al., "Establishment of a Clinical Threshold Cell Dose: Correlation Between CFU–Gm and Duration of Aplasia," AlphaMed Press, pp. 15–20. (1990).
Cioffi, J.A., et al., "Novell B219/OB receptor isoforms: Possible role of leptin in hematopoiesis and reproduction," Nature Medicine, vol. 2 (No. 5) :585–589 (May 1996).
Graf, L., et al., Identification of a Novel DNA Sequence Differentially Expressed Between Normal Human CD34+ CD38$^{10}$ Marrow Cells, Blood, vol. 86 (No. 2) :548–556 (Jul. 15, 1996).
Brashem–Stein, C., et al., "Ontogeny of Hematopoietic Stem Cell Development: Reciprocal Expression of CD33 and a Novel Molecule by Maturing Myeloid and Erythroid Progenitors," Blood, vol. 82 (No. 3) :792–799 (Aug. 1, 1993).
Lee, B.B., et al., "A Hematopoietic Organ–Specific 49–kD Nuclear Antigen: Predonminance in Immature Normal and Tumor Granulocytes and Detection in Hematopoietic Precursor Cells," Blood, vol. 87 (No. 6) :2283–2291 (Mar. 15, 1996).

(List continued on next page.)

Primary Examiner—Patrick J. Nolan
Assistant Examiner—Gerald R. Ewolt
(74) Attorney, Agent, or Firm—Cooley Godward LLP

(57) ABSTRACT

A hematopoietic progenitor cell antigen and reagents, notably antibodies, that specifically bind to the antigen are provided. Expression of the antigen is highly tissue specific. It is only detected on a subset of hematopoietic progenitor cells derived from human bone marrow, fetal bone marrow and liver, cord blood and adult peripheral blood. The subset of cells recognized by AC133 is CD34$^{bright}$ and contains substantially all of the CFU-GM activity present in the CD34$^+$ population. This highly specific distribution of AC133 makes it exceptionally useful as a reagent for isolating and characterizing human hematopoietic progenitor and stem cells. Cells selected for expression of AC133 antigen can be further purified by selection for other hematopoietic stem cell and progenitor cell markers.

9 Claims, 16 Drawing Sheets

OTHER PUBLICATIONS

Wognum, A.W., et al., "Distribution of Receptors for Granulocyte–Macrophage Colony–Stimulation Factor on Immature CD34 + Bone Marrow Cells, Differentiating Monomyeloid Progenitors, and Mature Blood Cell Subsets," Blood, vol. 84 (No. 3) :764–774 (Aug. 1, 1994).

Reisbach G., et al., "Characterization of hemopoietic cell populations from human cord blood expressing c–kit," 1993 International Society for Experimental Hematology, pp. 74–79.

Moretti, P. et al., "Identification of homeobox genes expressed in human haemopoietic progenitor cells," (1994) Elsevier Science B.V., pp. 213–219.

Sutherland and Keating, "The CD34 Antigen: Structure, Biology, and Potential Clinical Applications," J. of Hematotherapy, 1:115–129 (1992).

Civin and Gore, "Antigenic Analysis of Hematopeiesis: A Review," J. of Hematotherapy, vol. 2:137–144 (1993).

Kato and Radbruch, "Isolation and Characterization of CD34$^+$Hematopoietic Stem Cells, From Human Peripheral Blood by High–Gradient Magnetic Cell Sorting," Cytometry, vol. 14:384–392 (1993).

Database EMBL, entry HS057109, Accession No. R40057, May 28, 1995.

Database EMBL, entry HS499102, Accession No. R36499, May 5, 1995.

Database EMBL, entry HS59896, Accession No. R32598, May 4, 1995.

Database EMBL, entry HSGS04157, Accession No. D25789, Nov. 27, 1995.

Database EMBL, entry HSHBC4137, Accession No. D82259, Feb. 9, 1996.

Database EMBL, entry HSW25808, Accession No. W25808, May 10, 1996.

Olweus, J. et al., Blood 84 (Suppl. 1) 420A, Abstract #1666.(1994).

Olweus, J. et al., CD64/FcγRI Is a Granulo–monocytic Lineage Marker on CD34$^+$Hematopoietic Progenitor Cells, Blood 85 (9) :2402–2413 (1995).

* cited by examiner

FIG. 12 -1

| | | |
|---|---|---|
| CCAAGTTCTA CCTCATGTTT GGAGGATCTT GCTAGCT ATG GCC CTC GTA CTC GGC<br>                                                  Met Ala Leu Val Leu Gly<br>                                                   1                   5 | 55 |
| TCC CTG TTG CTG CTG GGG CTG TGC GGG AAC TCC TTT TCA GGA GGG CAG<br>Ser Leu Leu Leu Leu Gly Leu Cys Gly Asn Ser Phe Ser Gly Gly Gln<br>            10              15                  20 | 103 |
| CCT TCA TCC ACA GAT GCT CCT AAG GCT TGG AAT TAT GAA TTG CCT GCA<br>Pro Ser Ser Thr Asp Ala Pro Lys Ala Trp Asn Tyr Glu Leu Pro Ala<br>        25                  30                  35 | 151 |
| ACA AAT TAT GAG ACC CAA GAC TCC CAT AAA GCT GGA CCC ATT GGC ATT<br>Thr Asn Tyr Glu Thr Gln Asp Ser His Lys Ala Gly Pro Ile Gly Ile<br>    40                  45                  50 | 199 |
| CTC TTT GAA CTA GTG CAT ATC TTT CTC TAT GTG GTA CAG CCG CGT GAT<br>Leu Phe Glu Leu Val His Ile Phe Leu Tyr Val Val Gln Pro Arg Asp<br>55                  60                  65              70 | 247 |
| TTC CCA GAA GAT ACT TTG AGA AAA TTC TTA CAG AAG GCA TAT GAA TCC<br>Phe Pro Glu Asp Thr Leu Arg Lys Phe Leu Gln Lys Ala Tyr Glu Ser<br>                75                  80              85 | 295 |
| AAA ATT GAT TAT GAC AAG CCA GAA ACT GTA ATC TTA GGT CTA AAG ATT<br>Lys Ile Asp Tyr Asp Lys Pro Glu Thr Val Ile Leu Gly Leu Lys Ile<br>            90                  95              100 | 343 |
| GTC TAC TAT GAA GCA GGG ATT ATT CTA TGC TGT GTC CTG GGG CTG CTG<br>Val Tyr Tyr Glu Ala Gly Ile Ile Leu Cys Cys Val Leu Gly Leu Leu<br>        105                 110                 115 | 391 |
| TTT ATT ATT CTG ATG CCT CTG GTG GGG TAT TTC TTT TGT ATG TGT CGT<br>Phe Ile Ile Leu Met Pro Leu Val Gly Tyr Phe Phe Cys Met Cys Arg<br>    120                 125                 130 | 439 |
| TGC TGT AAC AAA TGT GGT GGA GAA ATG CAC CAG CGA CAG AAG GAA AAT<br>Cys Cys Asn Lys Cys Gly Gly Glu Met His Gln Arg Gln Lys Glu Asn<br>135                 140                 145             150 | 487 |
| GGG CCC TTC CTG AGG AAA TGC TTT GCA ATC TCC CTG TTG GTG ATT TGT<br>Gly Pro Phe Leu Arg Lys Cys Phe Ala Ile Ser Leu Leu Val Ile Cys<br>                155                 160                 165 | 535 |
| ATA ATA ATA AGC ATT GGC ATC TTC TAT GGT TTT GTG GCA AAT CAC CAG<br>Ile Ile Ile Ser Ile Gly Ile Phe Tyr Gly Phe Val Ala Asn His Gln<br>            170                 175             180 | 583 |
| GTA AGA ACC CGG ATC AAA AGG AGT CGG AAA CTG GCA GAT AGC AAT TTC<br>Val Arg Thr Arg Ile Lys Arg Ser Arg Lys Leu Ala Asp Ser Asn Phe<br>        185                 190                 195 | 631 |
| AAG GAC TTG CGA ACT CTC TTG AAT GAA ACT CCA GAG CAA ATC AAA TAT<br>Lys Asp Leu Arg Thr Leu Leu Asn Glu Thr Pro Glu Gln Ile Lys Tyr<br>    200                 205                 210 | 679 |
| ATA TTG GCC CAG TAC AAC ACT ACC AAG GAC AAG GCG TTC ACA GAT CTG<br>Ile Leu Ala Gln Tyr Asn Thr Thr Lys Asp Lys Ala Phe Thr Asp Leu<br>215                 220                 225             230 | 727 |

FIG. 12-2

| | | |
|---|---|---|
| AAC AGT ATC AAT TCA GTG CTA GGA GGC GGA ATT CTT GAC CGA CTG AGA<br>Asn Ser Ile Asn Ser Val Leu Gly Gly Gly Ile Leu Asp Arg Leu Arg<br>235 240 245 | | 775 |
| CCC AAC ATC ATC CCT GTT CTT GAT GAG ATT AAG TCC ATG GCA ACA GCG<br>Pro Asn Ile Ile Pro Val Leu Asp Glu Ile Lys Ser Met Ala Thr Ala<br>250 255 260 | | 823 |
| ATC AAG GAG ACC AAA GAG GCG TTG GAG AAC ATG AAC AGC ACC TTG AAG<br>Ile Lys Glu Thr Lys Glu Ala Leu Glu Asn Met [Asn Ser Thr] Leu Lys<br>265 270 275 | | 871 |
| AGC TTG CAC CAA CAA AGT ACA CAG CTT AGC AGC AGT CTG ACC AGC GTG<br>Ser Leu His Gln Gln Ser Thr Gln Leu Ser Ser Ser Leu Thr Ser Val<br>280 285 290 | | 919 |
| AAA ACT AGC CTG CGG TCA TCT CTC AAT GAC CCT CTG TGC TTG GTG CAT<br>Lys Thr Ser Leu Arg Ser Ser Leu Asn Asp Pro Leu Cys Leu Val His<br>295 300 305 310 | | 967 |
| CCA TCA AGT GAA ACC TGC AAC AGC ATC AGA TTG TCT CTA AGC CAG CTG<br>Pro Ser Ser Glu Thr Cys Asn Ser Ile Arg Leu Ser Leu Ser Gln Leu<br>315 320 325 | | 1015 |
| AAT AGC AAC CCT GAA CTG AGG CAG CTT CCA CCC GTG GAT GCA GAA CTT<br>Asn Ser Asn Pro Glu Leu Arg Gln Leu Pro Pro Val Asp Ala Glu Leu<br>330 335 340 | | 1063 |
| GAC AAC GTT AAT AAC GTT CTT AGG ACA GAT TTG GAT GGC CTG GTC CAA<br>Asp Asn Val Asn Asn Val Leu Arg Thr Asp Leu Asp Gly Leu Val Gln<br>345 350 355 | | 1111 |
| CAG GGC TAT CAA TCC CTT AAT GAT ATA CCT GAC AGA GTA CAA CGC CAA<br>Gln Gly Tyr Gln Ser Leu Asn Asp Ile Pro Asp Arg Val Gln Arg Gln<br>360 365 370 | | 1159 |
| ACC ACG ACT GTC GTA GCA GGT ATC AAA AGG GTC TTG AAT TCC ATT GGT<br>Thr Thr Thr Val Val Ala Gly Ile Lys Arg Val Leu Asn Ser Ile Gly<br>375 380 385 390 | | 1207 |
| TCA GAT ATC GAC AAT GTA ACT CAG CGT CTT CCT ATT CAG GAT ATA CTC<br>Ser Asp Ile Asp [Asn Val Thr] Gln Arg Leu Pro Ile Gln Asp Ile Leu<br>395 400 405 | | 1255 |
| TCA GCA TTC TCT GTT TAT GTT AAT AAC ACT GAA AGT TAC ATC CAC AGA<br>Ser Ala Phe Ser Val Tyr Val [Asn Asn Thr] Glu Ser Tyr Ile His Arg<br>410 415 420 | | 1303 |
| AAT TTA CCT ACA TTG GAA GAG TAT GAT TCA TAC TGG TGG CTG GGT GGC<br>Asn Leu Pro Thr Leu Glu Glu Tyr Asp Ser Tyr Trp Trp Leu Gly Gly<br>425 430 435 | | 1351 |
| CTG GTC ATC TGC TCT CTG CTG ACC CTC ATC GTG ATT TTT TAC TAC CTG<br>Leu Val Ile Cys Ser Leu Leu Thr Leu Ile Val Ile Phe Tyr Tyr Leu<br>440 445 450 | | 1399 |
| GGC TTA CTG TGT GGC GTG TGC GGC TAT GAC AGG CAT GCC ACC CCG ACC<br>Gly Leu Leu Cys Gly Val Cys Gly Tyr Asp Arg His Ala Thr Pro Thr<br>455 460 465 470 | | 1447 |

FIG. 12-3

| | | |
|---|---|---|
| ACC CGA GGC TGT GTC TCC AAC ACC GGA GGC GTC TTC CTC ATG GTT GGA<br>Thr Arg Gly Cys Val Ser Asn Thr Gly Gly Val Phe Leu Met Val Gly<br>475 480 485 | 1495 |
| GTT GGA TTA AGT TTC CTC TTT TGC TGG ATA TTG ATG ATC ATT GTG GTT<br>Val Gly Leu Ser Phe Leu Phe Cys Trp Ile Leu Met Ile Ile Val Val<br>490 495 500 | 1543 |
| CTT ACC TTT GTC TTT GGT GCA AAT GTG GAA AAA CTG ATC TGT GAA CCT<br>Leu Thr Phe Val Phe Gly Ala Asn Val Glu Lys Leu Ile Cys Glu Pro<br>505 510 515 | 1591 |
| TAC ACG AGC AAG GAA TTA TTC CGG GTT TTG GAT ACA CCC TAC TTA CTA<br>Tyr Thr Ser Lys Glu Leu Phe Arg Val Leu Asp Thr Pro Tyr Leu Leu<br>520 525 530 | 1639 |
| AAT GAA GAC TGG GAA TAC TAT CTC TCT GGG AAG CTA TTT AAT AAA TCA<br>Asn Glu Asp Trp Glu Tyr Tyr Leu Ser Gly Lys Leu Phe Asn Lys Ser<br>535 540 545 550 | 1687 |
| AAA ATG AAG CTC ACT TTT GAA CAA GTT TAC AGT GAC TGC AAA AAA AAT<br>Lys Met Lys Leu Thr Phe Glu Gln Val Tyr Ser Asp Cys Lys Lys Asn<br>555 560 565 | 1735 |
| AGA GGC ACT TAC GGC ACT CTT CAC CTG CAG AAC AGC TTC AAT ATC AGT<br>Arg Gly Thr Tyr Gly Thr Leu His Leu Gln Asn Ser Phe Asn Ile Ser<br>570 575 580 | 1783 |
| GAA CAT CTC AAC ATT AAT GAG CAT ACT GGA AGC ATA AGC AGT GAA TTG<br>Glu His Leu Asn Ile Asn Glu His Thr Gly Ser Ile Ser Ser Glu Leu<br>585 590 595 | 1831 |
| GAA AGT CTG AAG GTA AAT CTT AAT ATC TTT CTG TTG GGT GCA GCA GGA<br>Glu Ser Leu Lys Val Asn Leu Asn Ile Phe Leu Leu Gly Ala Ala Gly<br>600 605 610 | 1879 |
| AGA AAA AAC CTT CAG GAT TTT GCT GCT TGT GGA ATA GAC AGA ATG AAT<br>Arg Lys Asn Leu Gln Asp Phe Ala Ala Cys Gly Ile Asp Arg Met Asn<br>615 620 625 630 | 1927 |
| TAT GAC AGC TAC TTG GCT CAG ACT GGT AAA TCC CCC GCA GGA GTG AAT<br>Tyr Asp Ser Tyr Leu Ala Gln Thr Gly Lys Ser Pro Ala Gly Val Asn<br>635 640 645 | 1975 |
| CTT TTA TCA TTT GCA TAT GAT CTA GAA GCA AAA GCA AAC AGT TTG CCC<br>Leu Leu Ser Phe Ala Tyr Asp Leu Glu Ala Lys Ala Asn Ser Leu Pro<br>650 655 660 | 2023 |
| CCA GGA AAT TTG AGG AAC TCC CTG AAA AGA GAT GCA CAA ACT ATT AAA<br>Pro Gly Asn Leu Arg Asn Ser Leu Lys Arg Asp Ala Gln Thr Ile Lys<br>665 670 675 | 2071 |
| ACA ATT CAC CAG CAA CGA GTC CTT CCT ATA GAA CAA TCA CTG AGC ACT<br>Thr Ile His Gln Gln Arg Val Leu Pro Ile Glu Gln Ser Leu Ser Thr<br>680 685 690 | 2119 |
| CTA TAC CAA AGC GTC AAG ATA CTT CAA CGC ACA GGG AAT GGA TTG TTG<br>Leu Tyr Gln Ser Val Lys Ile Leu Gln Arg Thr Gly Asn Gly Leu Leu<br>695 700 705 710 | 2167 |
| GAG AGA GTA ACT AGG ATT CTA GCT TCT CTG GAT TTT GCT CAG AAC TTC<br>Glu Arg Val Thr Arg Ile Leu Ala Ser Leu Asp Phe Ala Gln Asn Phe<br>715 720 725 | 2215 |

FIG. 12-4

```
ATC ACA AAC AAT ACT TCC TCT GTT ATT ATT GAG GAA ACT AAG AAG TAT           2263
Ile Thr Asn Asn Thr Ser Ser Val Ile Ile Glu Glu Thr Lys Lys Tyr
        730             735                 740

GGG AGA ACA ATA ATA GGA TAT TTT GAA CAT TAT CTG CAG TGG ATC GAG           2311
Gly Arg Thr Ile Ile Gly Tyr Phe Glu His Tyr Leu Gln Trp Ile Glu
        745             750                 755

TTC TCT ATC AGT GAG AAA GTG GCA TCG TGC AAA CCT GTG GCC ACC GCT           2359
Phe Ser Ile Ser Glu Lys Val Ala Ser Cys Lys Pro Val Ala Thr Ala
        760             765                 770

CTA GAT ACT GCT GTT GAT GTC TTT CTG TGT AGC TAC ATT ATC GAC CCC           2407
Leu Asp Thr Ala Val Asp Val Phe Leu Cys Ser Tyr Ile Ile Asp Pro
775             780             785                 790

TTG AAT TTG TTT TGG TTT GGC ATA GGA AAA GCT ACT GTA TTT TTA CTT           2455
Leu Asn Leu Phe Trp Phe Gly Ile Gly Lys Ala Thr Val Phe Leu Leu
        795             800                 805

CCG GCT CTA ATT TTT GCG GTA AAA CTG GCT AAG TAC TAT CGT CGA ATG           2503
Pro Ala Leu Ile Phe Ala Val Lys Leu Ala Lys Tyr Tyr Arg Arg Met
        810             815                 820

GAT TCG GAG GAC GTG TAC GAT GAT GTT GAA ACT ATA CCC ATG AAA AAT           2551
Asp Ser Glu Asp Val Tyr Asp Asp Val Glu Thr Ile Pro Met Lys Asn
        825             830                 835

ATG GAA AAT GGT AAT AAT GGT TAT CAT AAA GAT CAT GTA TAT GGT ATT           2599
Met Glu Asn Gly Asn Asn Gly Tyr His Lys Asp His Val Tyr Gly Ile
        840             845                 850

CAC AAT CCT GTT ATG ACA AGC CCA TCA CAA CAT T GATAGCTGAT                  2643
His Asn Pro Val Met Thr Ser Pro Ser Gln His
855             860             865

GTTGAAACTG CTTGAGCATC AGGATACTCA AAGTGGAAAG GATCACAGAT TTTTGGTAGT         2703

TTCTGGGTCT ACAAGGACTT TCCAAATCCA GGAGCAACGC CAGTGGCAAC GTAGTGACTC         2763

AGGCGGGCAC CAAGGCAACG GCACCATTGG TCTCTGGGTA GTGCTTTAAG AATGAACACA         2823

ATCACGTTAT AGTCCATGGT CCATCACTAT TCAAGGATGA CTCCCTCCCT TCCTGTCTAT         2883

TTTTGTTTTT TACTTTTTTA CACTGAGTTT CTATTTAGAC ACTACAACAT ATGGGGTGTT         2943

TGTTCCCATT GGATGCATTT CTATCAAAAC TCTATCAAAT GTGATGGCTA GATTCTAACA         3003

TATTGCCATG TGTGGAGTGT GCTGAACACA CACCAGTTTA CAGGAAAGAT GCATTTTGTG         3063

TACAGTAAAC GGTGTATATA CCTTTTGTTA CCACAGAGTT TTTTAAACAA ATGAGTATTA         3123

TAGGACTTTC TTCTAAATGA GCTAAATAAG TCACCATTGA CTTCTTGGTG CTGTTGAAAA         3183

TAATCCATTT TCACTAAAAG TGTGTGAAAC CTACAGCATA TTCTTCACGC AGAGATTTTC         3243

ATCTATTATA CTTTATCAAA GATTGGCCAT GTTCCACTTG GAAATGGCAT GCAAAAGCCA         3303

TCATAGAGAA ACCTGCGTAA CTCCATCTGA CAAATTCAAA AGAGAGAGAG AGATCTTGAG         3363

AGAGAAATGC TGTTCGTTCA AAAGTGGAGT TGTTTTAACA GATGCCAATT ACGGTGTACA         3423
```

FIG. 12-5

```
GTTTAACAGA GTTTTCTGTT GCATTAGGAT AAACATTAAT TGGAGTGCAG CTAACATGAG    3483
TATCATCAGA CTAGTATCAA GTGTTCTAAA ATGAAATATG AGAAGATCCT GTCACAATTC    3543
TTAGATCTGG TGTCCAGCAT GGATGAAACC TTTGAGTTTG GTCCCTAAAT TGCATGAAA     3603
GCACAAGGTA AATATTCATT TGCTTCAGGA GTTTCATGTT GGATCTGTCA TTATCAAAAG    3663
TGATCAGCAA TGAAGAACTG GTCGGACAAA ATTTAACGTT GATGTAATGG AATTCCAGAT    3723
GTAGGCATTC CCCCCAGGTC TTTTCATGTG CAGATTGCAG TTCTGATTCA TTTG AATAAA   3783
AAGGAACTTG GAAAAAAAA A                                                3804
```

HUMAN HEMATOPOIETIC STEM AND PROGENITOR CELL ANTIGEN

CROSS REFERENCE TO RELATED APPLICATIONS

This application is a Continuation-In-Part of U.S. application Ser. No. 08/639,891, filed Apr. 26, 1996.

TECHNICAL FIELD

This invention relates to antigens expressed by hematopoietic stem cells and progenitor cells and to methods of using such antigens, especially for cell separation and purification.

BACKGROUND

The high turnover of mammalian blood cells requires a supply of hematopoietic stem cells that are able to give rise to other blood cell lineages. The immediate progeny of the hematopoietic stem cell are called progenitor cells, and are capable of giving rise to various cell types within one or more lineages, i.e. the erythroid, myeloid and lymphoid lineages. The stem cell and progenitor cell populations constitute only a small percentage of the total number of cells in bone marrow, fetal liver, etc. These populations are of immense interest because of their ability to repopulate the hematopoietic system.

A number of methods have been described in the literature for the purification or enrichment of hematopoietic stem cell and progenitor cell populations. There is significant commercial interest in these methods because hematopoietic progenitors have a number of clinical uses. Progenitor cell transplantation is currently used in conjunction with chemotherapy and radiation for the treatment of leukemia, breast cancer and other tumors. Frequently, autologous transplants are used to avoid the danger of graft rejection, but there is an increased risk of disease reappearance, due to the presence of tumor cells in the engrafting cell population. Transplantation of a more purified source of progenitor cells is therefore preferable.

There is also interest in the use of hematopoietic progenitor cells as a vehicle for gene therapy. Although not yet proven in the clinic, the longevity of hematopoietic stem cells and the dissemination of their progeny in the vasculature are desirable characteristics. A number of vectors, including several retrovirus and adenovirus based constructs, that can transfect hematopoietic stem cells have been described.

Proteins and other cell surface markers found on hematopoietic stem cell and progenitor cell populations are of great interest, as they are useful in preparing reagents for identification, separation and isolation of these populations and in the further characterization of these important cells. Although some antigens are now known that can be used in the identification and separation (positive and negative) of stem cells, such as (for example) the CD 34 antigen, which is found on stem cells but not on mature blood cells, there is a continued need for development of other antigens, particularly one that can simplify the identification and separation of desirable classes and subclasses of cells, especially hematopoietic stem cells and progenitor cells.

BACKGROUND LITERATURE

U.S. Pat. No. 5,061,620 describes a substantially homogeneous human hematopoietic stem cell composition and the manner of obtaining such composition. Stromal cell-associated hematopoiesis is described by Paul et al. (1991) *Blood* 77:1723–1733. The phenotype of stem cells with rhodamine staining is discussed in Spangrude and Johnson (1990) *P.N.A.S.* 87:7433–7437. Cell surface antigen expression in hematopoiesis is discussed in Strauss et al. (1983) *Blood* 61:1222–1231 and Sieff et al. (1982) *Blood* 60:703–713. Descriptions of pluripotential hematopoietic cells are found in McNiece et al. (1989) *Blood* 74:609–612 and Moore et al. (1979) *Blood Cells* 5:297–311. Characterization of a human hematopoietic progenitor cell capable of forming blast cell-containing colonies in vitro is found in Gordon et al. (1987) *J. Cell. Physiol.* 130:150–156 and Brandt et al. (1988) *J. Clin. Invest.* 82:1017–1027. The use of progenitor cells in transplantation is discussed in To et al. in *Progenitor Threshold in Transplantation* (ISBN 1-880854 17-1) pp. 15–20. Utilities for the cell compositions obtained using the methods and compositions of the invention are described in these publications, among others.

The use of high-gradient magnetic separation for the isolation of human hematopoietic progenitor cells is described in Thomas and Landsdorp (1992) in *Advances in Bone Marrow Purging* pp.537–544; and Kato and Radbruch (1993) *Cytometry* 14:384–392. Other methods of magnetic selection for human hematopoietic progenitor cells are described in Bigas et al. (1992) in *Advances in Bone Marrow Purging* pp.545–551; Oku et al. (1992) in *Advances in Bone Marrow Purging* pp. 553–560; and Hardwick et al. (1992) in *Advances in Bone Marrow Purging* pp. 583–589. High gradient magnetic cell sorting is described in Miltenyi et al. (1990) *Cytometry* 11:231–238. Molday, U.S. Pat. No. 4,452, 773 describes the preparation of magnetic iron-dextran microspheres and provides a summary describing the various means of preparation of particles suitable for attachment to biological materials.

SUMMARY OF THE INVENTION

Methods and compositions are provided for the enrichment and characterization of human hematopoietic progenitor and stem cells. An antigen has been identified, referred to here as the AC133 antigen, that is present on stem cells and on progenitor cells and that can be used for the identification and/or separation of these important cells from the vast majority of cells present in a biological (or other) source of hematopoietic cells. Novel antigen compositions and reagents that react with them, such as antibodies, are provided for use in the methods of the invention and for the further investigation of hematopoietic progenitor and stem cell biology. For example, hematopoietic cells can be obtained from various sources, including fetal and adult bone marrow, cytokine mobilized peripheral blood cells, and fetal liver, and can be separated using reagents and methods of the invention.

BRIEF DESCRIPTION OF THE DRAWINGS

The invention now being generally described, the same will be better understood by reference to the following description of specific embodiments together with the figures that form part of the current specification, wherein:

In FIG. 5A the x axis represents CD38-FITC staining, and the y axis represents HPCA2-PE staining. In FIGS. 5B, 5C and 5D, the x axis represents staining with HPCA2-FITC. The y axis in FIG. 5B represents cell staining with anti-HLA-DR-PE. The y axis in FIG. 5C represents cell staining with anti-CD90-PE. The y axis in FIG. 5D represents cell staining with anti-CD117-PE. The numbers represent the percent of total cells that fall within the boxed gates.

FIG. 12 is a chemical formula showing DNA (SEQ ID NO:1) and amino acid (SEQ ID NO:2) sequences for the AC133 antigen.

DESCRIPTION OF SPECIFIC EMBODIMENTS

Figure 1:
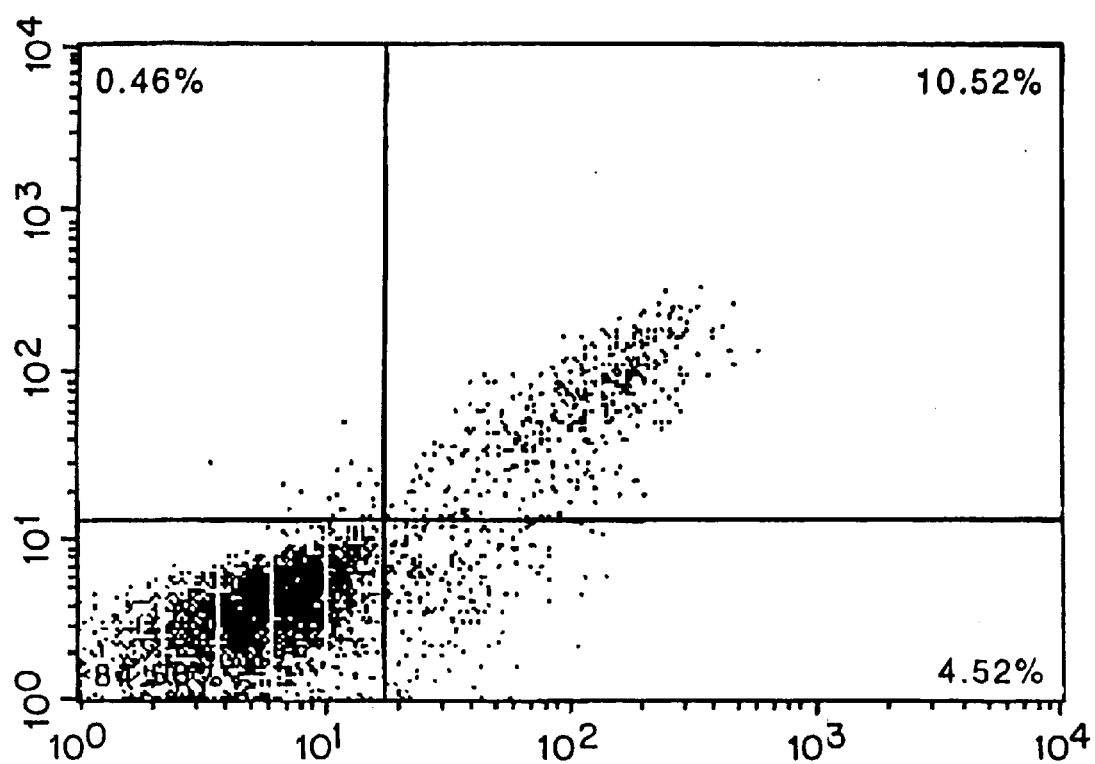
FIG. 1 shows a dot-plot from fluorescence activated cell sorting (FACS) analysis of fetal liver cells. The y axis represents cell staining with AC133 antibody conjugated to phycoerythrin (PE). The cells were counterstained with HPCA2-FITC (anti-CD34). The numbers represent the percent of total cells that fall within the quadrants.

Methods and compositions are provided that have use in the enrichment and/or characterization of human hematopoietic stem cells and/or progenitor cells. The immediate progeny of the hematopoietic stem cell, called here "progenitor" cells, are capable of giving rise to various cell types within one or more lineages. In the present invention, stem cells and/or a sub-set of progenitor cells (i.e., CFU-GM cells that are needed for short-term ingraftinent) can be identified or selected through the use of reagents that specifically bind to a newly discovered antigen referred to here as the AC133 antigen (Ag) that is highly specific for these cells. The high tissue specificity of AC133 antigen expression is particularly advantageous during enrichment for highly purified progenitor cell populations. An AC133-positive cell population is highly enriched for cells that are active in assays measuring progenitor cell activity, particularly in the CFU-GM activity. The subset of cells that is AC133 negative and CD34 positive is enriched for BFU-E activity, a measure of erythroid-committed progenitor cell activity.

Reagents that specifically bind to the AC133 antigen include without limitation physiological ligands, synthetic ligands, polyclonal antibodies, and monoclonal antibodies. An AC133 monoclonal antibody is any monoclonal antibody which interacts specifically with the AC133 cell antigen expressed on a subset of hematopoietic progenitor cells derived from human bone marrow, fetal bone marrow and liver, cord blood and adult peripheral blood. The subset of progenitor cells recognized by antibodies directed to AC133 are $CD34^{bright}$ and contains substantially all of the CFU-GM activity present in the $CD34^+$ subset (as well as those cells that are still stemcells collected in a collection of progenitor cells). For purposes of transplantation, cells active in CFU-GM are of particular interest because they provide for production of neutrophils. Use of an AC133 antibody allows positive immunoselection of hematopoietic progenitor cell populations, as well as the phenotypic analysis of progenitor cell populations using flow cytometry. In particular, an antibody against AC133 recognizes not just CFU-GM cells, which are needed for short-term engraftment and protection from sepsis, but also primitive long-term re-populating cells that are necessary for long-term engraftment. Cells selected for expression of AC133 antigen can then be further purified and/or separated by selection for other hematopoietic stem cell and progenitor cell markers.

As outlined below in detail, molecules of interest in the various methods of the invention include the AC133 antigen itself, reagents that specifically bind to AC133 or a fragment thereof, AC133 complexed to a ligand, an AC133-ligand complex wherein the ligand is an antibody, nucleic acid sequences encoding the AC133 antigen, and population of cells that express the AC133 antigen or any of its fragments. The AC133 antigen can be isolated from natural sources or produced using recombinant DNA technology. The nucleic acids can be cDNA, RNA, a genomic sequence, or a synthetic sequence comprising the coding sequence by itself or in conjunction with transcriptional regulatory regions and other sequences found in expression and/or cloning vectors. The AC133 Ag itself can be obtained in a purified form by isolation from cells, which can be identified as positive by AC133 antibody binding using affinity binding methods known in the art. Positive identification is available by proteolytic digestion of cell membrane proteins and comparison of sequences to the protein sequence for AC133 set out in FIG. 12.

mAb AC133 is an antibody with specificity for a novel cell surface antigen that is expressed on bright $CD34^+$ cells. The antigen is expressed on a subset of hematopoietic progenitor cells derived from human bone marrow, fetal bone marrow and liver, cord blood, and adult peripheral blood. mAb AC133 can be used in a magnetic bead system to immunoselect hematopoietic progenitor cell populations, resulting in potential therapeutic benefit, as well as in the phenotypic analysis of progenitor cell populations using flow cytometric techniques. To further characterize the nature of this novel molecule, the AC133 antigen was purified by immunoaffinity chromatography. The AC133 antigen consists of a single polypeptide chain with a reduced molecular weight of about 120 kD, and comprises a glycoprotein with an about 20-kDa N-glycosidic-linked polysaccharides. The reduced AC133 antigen is recognized by mAb AC133, suggesting a linear epitope or a sugar epitope.

It will be recognized by those experienced in the field of glycoproteins that such molecules are not expected to have exactly identical sugar structures because of the enzymatic nature of sugar synthesis, which occurs without the template (i.e., messenger RNA) that exists for peptide synthesis, although similarities will certainly exist among the sugar structures in a collection of AC133 molecules because of synthesis from the same starting peptide structure. Accordingly, "AC133 antigen" refers to proteins having the peptide structure shown in FIG. 12 (discussed below) with sugar structures attached at glycoslyation sites. Because of the natural variations in sugar structures, a range of molecular weights for glycosylated molecules is also to be expected and comes within the scope of the present invention. In the case of AC133 antigen, there appears to be relatively low variation in the structure and size of the attached sugar residues, compared to other known proteins. Molecular weight of AC133 is typically found to be in the range of 115 to 127 kD, regardless of the details of the experimental technique used to measure molecular weight.

Figure 13:
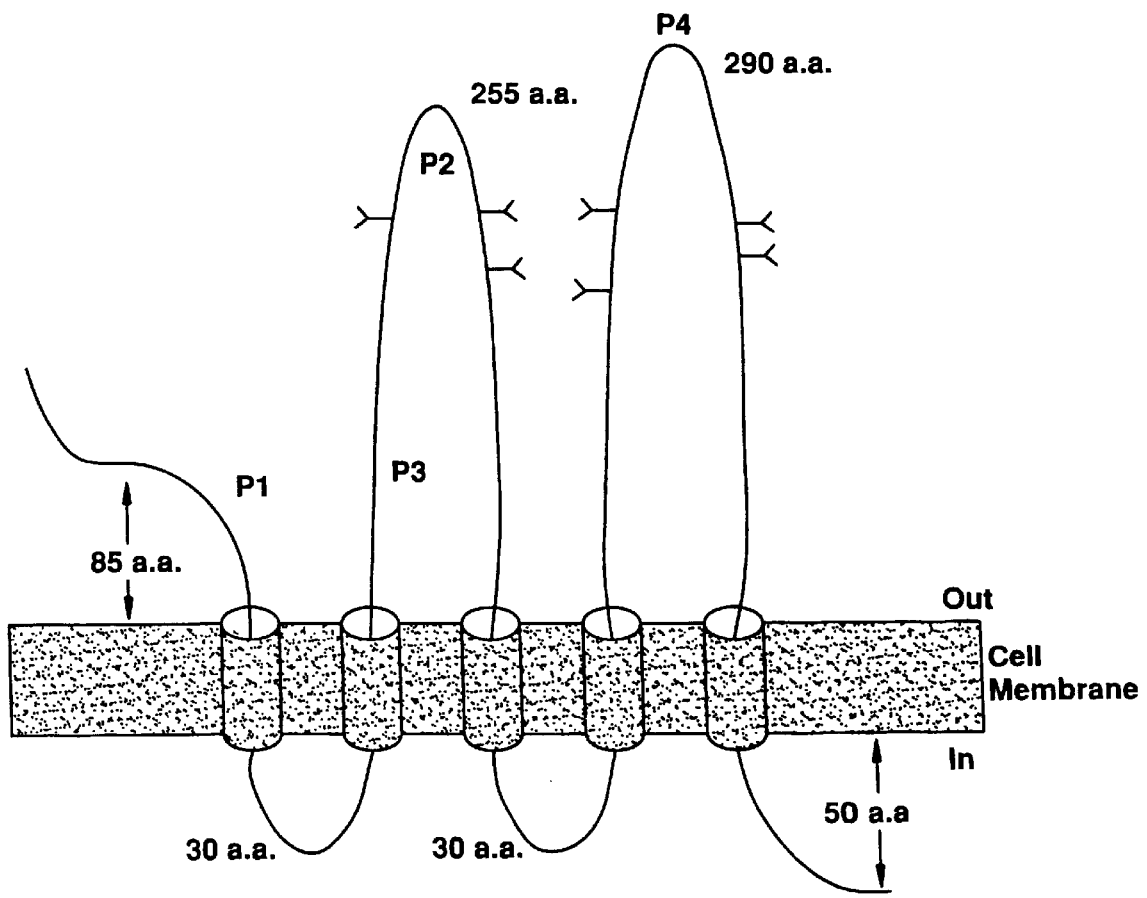
FIG. 13 is a schematic diagram of the transmembrane and other regions of the AC133 antigen.

The purified AC133 antigen was digested with lysyl endopeptidase to generate peptides that were isolated by reverse phase HPLC and sequenced by Edman degradation. These peptides were used to design degenerate oligonucleotides used in the polymerase chain reaction with a WERI-Rb-1 cDNA library template. This technique yielded 1.7 kB of unambiguous sequence which was then used to isolate the entire cDNA clone. This cDNA encodes a single open reading frame of 2598 nucleotides, and predicts a 865 amino acid protein with a molecular weight of 96.8 kDa, which corresponds with the about 90 kDa molecular weight found for the deglycosylated antigen. Hydrophobicity and transmembrane helicity analysis suggests the presence of five transmembrane domains, resulting in two large extracellular loops. There are a total of 8 consensus sequences for sites of N-linked glycosylation, all on the two large (260 and 290 a.a.) loops supporting our proposed structural model with two large extracellular loops and a 50 amino acid C-terminal cytoplasmic tail. A truncated version of the AC133 antigen missing the cytoplasmic tail is still recognized by mAb AC133. There are consensus sequences for a leucine zipper motif in both extracellular loops, which can be involved in receptor interaction with its physiological ligand. As shown in FIG. 13, the AC133 antigen appears as a 5-transmembrane protein ("5TM protein") with an extracellular N-terminus and a cytoplasmic C-terminus.

Families of 4TM (also called tetraspan), 7TM, and 11TM proteins have been characterized in the literature. While the function of the tetraspan family is not known, the 7TM proteins are generally believed to be G-protein coupled receptors binding chemotactic agonists, and 11TM proteins represent a family of ion-channel receptors. However, a 5TM molecule has not previously been described, and the structure of the AC133 antigen differs markedly from known 7 TM family members with respect to molecular weight and size of extracellular loops. Additionally, the AC133 antigen does not share sequence homology with 4TM or 7TM proteins, while family members do share significant homology with each other, particularly within the transmembrane domains.

Short fragments of the AC133 gene are present in Genbank as EST's (expressed sequence tags), such as adult retina, pancreatic islets and fetal brain. Expression of the AC133 antigen, however, appears to be limited to primitive hematopoietic stem cells and some neural-crest-derived tissues. AC133 antigen is also expressed on NT-2 teratocarcinoma cells; however expression is lost as these cells terminally differentiate into neurons. The interaction of the physiological ligand with the AC133 antigen (receptor) can provide for intracellular signalling.

The original monoclonal antibody discovered to the AC133 antigen is one of a panel of antibodies which defines a novel antigen of approximately Mr 120,000 which is selectively expressed on $CD34^{bright}$ human hematopoietic stem and progenitor cells. $CD34^{bright}$ cells support long-term B cell lymphopoiesis and myelopoiesis in vitro and mediate T, B, myelomonocytic and megakaryocytic repopulation in vivo. $CD34^{dim}$ cells have failed to provide long-term hematopoietic activity in vitro or in vivo. The $CD34^{bright}$ population contains all of the primitive stem cell activity and therefore is the population of choice for further studies in hematopoietic stem cell transplantation and gene therapy. AC133 antibody provides a means for the positive selection and phenotypic analysis of hematopoietic stem cells and a subset of committed progenitor cells. The original specific antibody AC133, a murine $IgG_1$ antibody, was elicited from mice immunized with urified $CD34^+$ human progenitor cells. In order to determine the precise antigen phenotype of AC133 positive cells, AC133 and CD34 double positive cells were examined in fetal liver, fetal and adult bone marrow, cord blood and peripheral blood using 3 and 4 color FACS analysis. The subset recognized by AC133 antibody in all tissues are $CD34^{bright}$, $CD38^{-/+}$, $HLA-DR^{+/-}$. The $CD90^+$, $CD117^+$ and $CD109^+$ stem cell populations are included within the AC133 positive population. Typically AC133 stains 20–60% of all $CD34^+$ cells, a population which contains all the non-lineage committed $CD34^+$ population as well as CD34+ cells committed to the granulocyte/monocytic pathway. AC133 antigen expression has not been demonstrated on peripheral blood mononuclear cells, granulocytes, platelets or umbilical vein-derived endothelial cells by standard FACS procedures. FACS analysis on a panel of 50 human cell lines shows that only 2 retinoblastoma cell lines, Y79.1 and WERI-Rb-1, express AC133 antigen, along with NT-2 teratocarcinoma cells. Transplantation of AC133 positive cells into fetal sheep has demonstrated the engrafting capability of selected cells, and human cells which have homed to the fetal sheep bone marrow have been harvested and shown to engraft secondary recipients, proving the long term repopulating potential of selected cells. The AC133 gene codes for a polypeptide consisting of 865 aa with a predicted size of 96.8 kDa. This protein has a unique structure, traversing the membrane 5 times. The AC133 antigen therefore defines a new class of mammalian 5TM membrane proteins. Together these data demonstrate that AC133 provides an alternative antigen system for the identification and separation of hematopoietic stem cells.

Antibodies that selectively bind to stem cells and/or progenitor cells are of particular interest. Antibodies to AC133 Ag can be obtained by immunizing a xenogeneic immunocompetent mammalian host (such as a murine, rodentia, lagomorpha, ovine, porcine, or bovine, host) with human hematopoietic progenitor cells. The choice of a particular host is primarily one of convenience. A suitable progenitor cell population for immunization is obtained by isolating $CD34^+$ cells from cytokine-mobilized peripheral blood, bone marrow, fetal liver, or other source of progenitor cells. The cells can be incubated with phytohemagglutinin prior to their use as an immunogen.

Immunizations are performed in accordance with conventional techniques, where the cells can be injected subcutaneously, intramuscularly, intraperitoneally, intravascularly into a host. Normally, from about $10^6$ to $10^8$ cells will be used, which can be divided into 1 or more injections, usually not more than about 8 injections, over a period of from about one to three weeks. The injections can occur with or without adjuvant; examples of adjuvant include complete or incomplete Freund's adjuvant, specol, and alum.

In a preferred embodiment, contralateral immunization is used, as described in the examples below. This method relies on the trafficking ability of immune lymphocytes to home to the site of antigen stimulation. The animals are pre-immunized at a localized site on one side of the body, such as a left footpad, with cells that express many immunodominant but irrelevant antigens. Various mature hematopoietic cells can be used for this purpose. The immunogen of interest is injected at a localized site on the opposite side of the animal. Lymphocytes pre-immunized with and responding to irrelevant antigens are decoyed to the left-hand draining lymph nodes, while the lymphocytes responding to the immunogen of interest will be present in the right-hand draining lymph nodes, e.g. the popliteal lymph nodes for footpad injection. This popliteal lymph node can be used as a source of cells for fusion.

After completion of the immunization schedule, the antiserum can be harvested in accordance with conventional techniques to provide polyclonal antisera specific for the surface membrane proteins of hematopoietic progenitor cells, including AC133 Ag. Lymphocytes can then be harvested from the appropriate lymphoid tissue, e.g. spleen or draining lymph node, and fused with an appropriate fusion partner, usually a myeloma line, to produce a hybridoma secreting a specific monoclonal antibody. Screening clones of hybridomas for the antigenic specificity of interest can be performed in accordance with conventional methods.

Of particular interest are the specific monoclonal antibody AC133 described in the Examples below; other antibodies (both monoclonal and polyclonal) that bind to the AC133 antigen, especially cross-reactive antibodies (i.e., those which bind to the same epitope, and substantially inhibit simultaneous binding); species analogs thereof; binding fragments thereof; and conjugates thereof. A deposit of a murine hybridoma cell line that expresses an antibody to the AC133 antigen was made at the American Type Culture Collection, 10801 University Boulevard, Manassas Va. 20110, on Apr. 23, 1997, and given the ATCC designation HB12346. These antibodies are capable of immunoselection for the hematopoietic subset of interest.

It is known that antibodies can be produced as a single chain instead of a normal multimeric structure. Single chain antibodies are described in Jost et al. (1994) *J.B.C.* 269:26267–73, and in numerous other publications. DNA sequences encoding the variable region of the heavy chain and the variable region of the light chain are ligated to a spacer encoding at least about 4 amino acids of small neutral amino acids, including glycine and/or serine. The protein encoded by this fusion allows assembly of a functional variable region that retains the specificity and affinity of the original antibody.

Methods of humanizing antibodies are also known in the art. A humanized antibody can be the product of an animal having transgenic, human, immunoglobulin-constant-region genes (see for example International Patent Applications WO 90/10077 and WO 90/04036). Alternatively, the antibody of interest can be engineered by recombinant DNA techniques to substitute the CH1, CH2, CH3, hinge domains, and/or the framework residues with the corresponding human sequence (see WO 92/02190).

The use of Ig cDNA for construction of chimeric immunoglobulin genes is known in the art (Liu et al. (1987) *P.N.A.S.* 84:3439 and (1987) *J. Immunol.* 159:3521). In these techniques mRNA is isolated from a hybridoma or other cell producing the antibody and used to produce cDNA. The cDNA of interest can be amplified by the polymerase chain reaction using specific primers (U.S. Pat. Nos. 4,683,195 and 4,683,202). Alternatively, a library can be made and screened to isolate the sequence of interest. The DNA sequence encoding the variable region of the antibody is then fused to human constant region sequences. The sequences of human constant region genes can be found in Kabat et al. (1991) *Sequences of Proteins of Immunological Interest,* N.I.H. publication no. 91–3242. Human C region genes are readily available from known clones. The chimeric, humanized antibody can then be expressed by conventional methods.

Antibody fragments, such as Fv, F(ab')$_2$ and Fab fragments, can be prepared by cleavage of the intact antibody, e.g. by protease or chemical cleavage. Alternatively, a truncated gene can be designed. For example, a chimeric gene encoding a portion of the F(ab')$_2$ fragment could include DNA sequences encoding the CH1 domain and hinge region of the H chain, followed by a translational stop codon to yield a truncated antibody fragment.

Antibodies to the AC133 antigen bind to a protein that has an apparent molecular weight (under Western blot conditions from reducing SDS-PAGE gels, based on commercially available standards) of about 120 kD, and generally appears to be in the range of about 115 to 127 kD. The antibody appears to recognize a sugar epitope, as AC133 antibody cannot be immunoprecipitated from tunicamycin-treated WERI-Rb-1 cells. The AC133 antigen is expressed on a subset of CD34$^+$ cells, but is absent on endothelium and fibroblasts. Included in the population of AC133-positive cells are HLA-DR$^+$, CD90$^+$ and CD117$^+$ progenitor cells (the antigen formerly known as CD90$^+$ is now known as CD90$^+$; both DR positive and negative as well as CD38 positive and negative cells are included in this population). This population contains substantially all of the hematopoietic stem activity present in the CD34$^+$ subset of hematopoietic cells.

Reagents that specifically bind to the AC133 antigen are not limited to antibodies. Any of numerous methods known in the art to detect the binding of one species to another can be used to assay for the presence of an AC133 antigen-binding reagent. One universally adaptable assay involves distribution of radioactivity between soluble and solid phases can be detected using radioactively labeled test compounds and AC133 antigen attached to a solid phase. AC133 antigen can be attached, for example, to a solid phase in a column, and a tritium- or $^{14}$C-labelled test compound in a physiological buffer can be passed through the column. Bound radioactivity can be detected directly on the column or by subtraction of radioactivity in the soluble phase passing through the column from the applied radioactivity. Binding affinity can be detected by measuring levels of bound radioactivity at different concentrations of test compound after allowing sufficient time for binding to equilibrate. Specificity of binding for AC133 can be detected by determining whether test compounds that bind to AC133 also bind to antigens present on mature blood cells (or other antigens of interest in a preselected assay medium). Especially preferred ligands are those that are selective for AC133 with less than 10%, preferably less than 5%, cross-reactivity with any antigen present on mature blood cells. Crossreactivity can be measured by any standard technique and preferably is measured by a competitive binding assay between pure AC133 antigen, the ligand to be tested, and the suspected crossreactive antigen using a concentration of AC133 antigen and test ligand where the ligand half-saturates binding to AC133. Most preferably, crossreactivity is measured at a concentration of AC133 antigen that half saturates monoclonal antibody ATCC HB12346 when the antibody is present at a concentration of 50 ng/100 µl.

Once a reagent is identified that specifically binds to AC133, the reagent (in its radioactively labeled form, in a non-radioactive form modified to contain another label, or in certain uses in unlabeled form) can be used in various assays or biological uses that call for the binding of a reagent to AC133, such as fluorescent staining, cell separation, or cell differentiation, either in vivo and in vitro. For example, immunoselection with an antibody against AC133 provides a means of purifying hematopoietic progenitor and stem cells. The antibodies also find use in diagnostics to detect or enumerate hematopoietic progenitor cells, in dividing the CD34 positive population into functionally distinct sub-populations, in isolation of progenitor cells, and in preparation of progenitors to produce mature blood cells. Biological samples (e.g. blood or derivatives thereof, biopsies, and synovial fluid) can be assayed for the presence of cells expressing the surface molecule bound by the subject antibodies. For example, assays can be performed on cell lysates, intact cells, or frozen sections in order to distinguish different types of cells.

The subject antibodies and other reagents that specifically bind to AC133 are useful for the preparation of substantially pure human hematopoietic progenitor and stem cells. A subset of progenitor cells can be separated from other hematopoietic cells on the basis of AC133 binding and can be further separated from each other by binding to other surface markers known in the art. Sources of hematopoietic cells include fetal or adult bone marrow; fetal liver; umbilical cord blood; and peripheral blood, particularly cytokine mobilized peripheral blood (see, for example, Campos et al. (1993) *Leukemia* 7:1409–15 and Grigg et al. (1993) *Bone Marrow Transplant* 11, Suppl 2:23–9).

Human stem cells have been reported to have the phenotype $CD34^{bright}$; $HLA-DR^+$; $CD38^{dim/negative}$; $CD117(c\text{-}kit)^{dim}$; $CD90(Thy\text{-}1)^+$; and to lack expression of a variety of lineage specific markers, including CD3, CD4, CD7, CD8, CD14, CD15, and CD19. A negative designation indicates that the level of staining is at or below the brightness of an isotype-matched negative control. A dim designation indicates that the level of staining may be near the level of a negative stain, but may also be brighter than an isotype matched control.

Procedures for separation include magnetic separation using antibody-coated magnetic beads and affinity chromatography or "panning" using antibody attached to a solid matrix (e.g. plate). Techniques providing accurate separation include fluorescence-activated cell sorters, which can have varying degrees of sophistication, such as having multiple color channels, low angle and obtuse light scattering detecting channels, or impedance channels. Dead cells can be eliminated by selection with dyes associated with dead cells e.g., (propidium iodide, LDS). Red blood cells can be removed by (for example) elutriation, hemolysis, or Ficoll-Paque gradients. Any technique can be employed that is not unduly detrimental to the viability of the selected cells.

Conveniently, antibodies can be conjugated with labels for a number of different purposes: e.g., magnetic beads to allow for ease of separation of a particular cell type; biotin, which binds with high affinity to avidin or streptavidin; fluorochromes, which can be used with a fluorescence activated cell sorter; haptens; and the like. Multi-color analyses can be employed with a FACS or in a combination of immunomagnetic separation and flow cytometry. Multi-color analysis is of interest for the separation of cells based on multiple surface antigens: e.g., $AC133^+$, $CD90^+$ or $CD117^+$, $AC133^-$, or $CD34^+$. Fluorochromes which find use in a multi-color analysis include phycobiliproteins, e.g. phycoerythrin and allophycocyanins; fluorescein, and Texas red.

In one embodiment of the invention, an anti-AC133 antibody is directly or indirectly conjugated to a magnetic reagent, such as a superparamagnetic microparticle (microparticle). Direct conjugation to a magnetic particle is achieved by use of various chemical linking groups as known in the art. For example, antibody can be coupled to the microparticles through side chain amino or sulfhydryl groups and heterofunctional cross-linking reagents. A large number of heterofunctional compounds are available for linking to entities. A preferred linking group is 3-(2-pyridyldithio)propionic acid N-hydroxysuccinimide ester (SPDP) or 4-(N-maleimidomethyl)-cyclohexane-1-carboxylic acid N-hydroxysuccinimide ester (SMCC) with a reactive sulfhydryl group on the antibody and a reactive amino group on the magnetic particle.

Alternatively, an anti-AC133 antibody is indirectly coupled to magnetic particles. The antibody is directly conjugated to a hapten, and hapten-specific, second-stage antibodies are conjugated to the particles. Suitable haptens include digoxin, digoxigenin, FITC, dinitrophenyl, nitrophenyl, avidin, and biotin. Methods for conjugation of the hapten to a protein are known in the art, and kits for such conjugations are commercially available.

For separation or identification of stem cells or progenitor cells, an antibody is added to a hematopoietic cell sample. The amount of an anti-AC133 antibody necessary to bind a particular cell subset is empirically determined by performing a test separation and analysis. The cells and an anti-AC133 Ab are incubated for a period of time sufficient for complexes to form, usually at least about five minutes, more usually at least about 10 minutes, and usually not more than one hour, more usually not more than about 30 minutes.

The cells can additionally be incubated with antibodies or binding molecules specific for cell-surface markers known to be present or absent on hematopoietic progenitor or stem cells. For example, CD90, CD117 and HLA-DR are useful in the positive selection of stem cells. Various markers known to be absent on stem cells, such as CD3, CD4, CD8, CD14, CD15, and CD19, can be used for negative selection. The labeled cells are separated in accordance with the specific antibody preparation. Fluorochrome-labeled antibodies are useful for FACS separation and magnetic particles for immunomagnetic selection or particularly high gradient magnetic selection (HGMS). Exemplary magnetic separation devices are described in WO/90/07380, PCT/US96/00953 and EP 438,520, herein incorporated by reference.

The purified cell population can be collected in any appropriate medium. Various media are commercially available and can be used, including Dulbecco's Modified Eagle Medium (DMEM), Hank's Basic Salt Solution (HBSS), Dulbecco's phosphate buffered saline (DPBS), RPMI, Iscove's modified Dulbecco's medium (IMDM), and phosphate buffered saline (PBS) with 5 mM EDTA, any of which can be supplemented with fetal calf serum (FCS), bovine serum albumin (BAD), or human serum albumin (HSA).

Compositions highly enriched for human hematopoietic progenitor and/or stem cells (depending on the source of cells) are achieved in this manner in a single step. The desired cells will be at or about 80% or more of the cell composition, and preferably be at or about 90% or more of the cell composition. Specific populations of interest include $AC133^+$ cells, which are characterized as $CD34^{bright}$ and $HLA-DR^{+/-}$. This population can be further selected for those cells that are $CD90^+$, $CD117^+$ and/or $CD38^{dim}$. Functionally these cells are highly enriched for CFU-GM activity and for long-term re-populating cells. Another population of interest is $CD133^-$ and $CD34^+$, which is enriched for BFU-E activity. The use of the subject antibodies for purification are advantageous over the use of CD34, because AC133 is expressed by a more restricted population of cells, thereby permitting a more enriched subset for the specific activity of interest.

Once the desired cells have been isolated, they can be propagated by growing in conditioned medium from stromal cells, co-culturing with such stromal cells, or in media comprising maintenance factors supporting the proliferation of such progenitor cells e.g., stem cell factor or combinations of interleukins. The medium employed for culturing cells is conveniently a defined enriched medium, such as IMDM or a mixture of IMDM and RPMI 1640, and will generally be composed of salts, amino acids, vitamins, $5 \times 10^{-5}$ M β-mercaptoethanol, streptomycin/penicillin and 10% fetal calf serum, and can be changed from time to time, generally at least once to twice per week.

The subject cell compositions find use in a variety of ways. They can be used to reconstitute an irradiated host and/or a host subject to chemotherapy. By providing for maturation, proliferation and differentiation into one or more selected lineages through specific different growth factors the progenitor cells can be used as a source of committed cells. Such factors as erythropoietin, colony stimulating factors (e.g., GM-CSF, G-CSF or M-CSF), interleukins (e.g. IL-1, -2, -3, -4, -5, -6, -7, -8, -9, or -10), or the like, or stromal cells can be used to influence the growth and differentiation of progenitor cells.

The cells can also be used in the isolation and evaluation of factors associated with the differentiation and maturation of hematopoietic cells, including reagents that specifically bind to the AC133 antigen. Thus, the cells can be used in assays to determine the activity of media, such as conditioned media; to evaluate fluids for growth factor activity or involvement with dedication of lineages; or the like.

The cells can be used for the treatment of genetic diseases. Genetic diseases associated with hematopoietic cells can be treated by genetic modification of autologous or allogeneic stem cells to correct a genetic defect or treat to protect against disease, e.g., HIV. For example, diseases such as β-thalassemia, sickle cell anemia, adenosine deaminase deficiency, recombinase deficiency, or recombinase regulatory gene deficiency can be corrected by introduction of the wild-type gene into the subject cells, either by homologous or random recombination. Alternatively, normal allogeneic progenitor cells can be transplanted. Diseases other than those associated with hematopoietic cells can also be treated, where the disease is related to the lack of a particular secreted product such as hormone, enzyme, interferon, factor, or the like.

The cells can be frozen at liquid nitrogen temperatures and stored for long periods of time, as they can be thawed and reused. The cells will usually be stored in 5% DMSO and 95% fetal calf serum. Once thawed, the cells can be expanded by use of growth factors or stromal cells associated with stem cell proliferation and differentiation.

The AC133 antigen can be obtained in substantially pure form from either natural sources or by recombinant techniques. From natural sources, the antigen-positive cells are lysed and passed through an affinity column of anti-AC133 monoclonal antibody. Hematopoietic progenitor cells can be isolated from natural sources by conventional separation techniques, or cell lines described in the experimental section can be used as a source of antigen. The affinity-purified protein is eluted from the affinity column with an appropriate salt solution or aqueous/organic gradient, such as acetonitrile or ethanol, usually in the presence of a low acid concentration, e.g., 0.1–1 percent trifluoroacetic acid. The eluted protein is then further purified by chromatography, electrophoresis, or the like in accordance with conventional techniques.

The examples below describe the use of a monoclonal antibody to purify the AC133 antigen by affinity chromatography resulting in greater than 95% pure AC133 antigen. Peptides of such a purified preparation can be prepared and isolated for sequence analysis, as a result of which nucleic acid probes can be designed for the isolation of AC133 gene sequences. The gene sequence of AC133 set forth herein (FIG. 12) allows the antigen to be obtained by recombinant techniques. For example, total RNA is isolated from cells that have been shown by antibody binding to express the targeted protein. Residual DNA is removed in accordance with conventional techniques, and the polyadenylated RNA can be purified further, for example on oligo-dT sepharose or by gel chromatography. cDNA is then prepared in accordance with conventional techniques using reverse transcriptase (see Sambrook et al., supra and the Examples below). The cDNA is then introduced into an appropriate cloning system, such as λ gt11, where the cDNA is expressed. The phage plaques can then be screened using the subject antibodies, or by employing polyclonal antisera. Alternatively, a cloning system can be used which allows probing with nucleic acid sequences derived from the AC133 antigen protein sequence. The cDNA inserts are then subcloned into other vectors, as desired. The cDNA can be used for further probing of the cDNA library for a complete transcript. Alternatively, the cDNA sequence can be used to probe a genomic library to identify the genomic gene encoding the subject proteins (See, for example, Molecular Cloning: A Laboratory Manual, 2nd ed., J. Sambrook, E. F. Fritsch, T. Maniatis, CSHL, Cold Spring Harbor, N.Y., 1989).

DNA of the invention includes the nucleotide sequences encoding the AC133 protein or fragments thereof, as well as adjacent 5' and 3' non-coding nucleotide sequences involved in the regulation of expression of the protein encoded by the genes, and will include up to about the length of the mature mRNA or genomic DNA. Thus, the present invention provides an isolated nucleic acid molecule, in which the molecule comprises (1) a first sequence having an amino acid coding region for AC133 as set forth in FIG. 1 (SEQ ID NO:1); (2) a second sequence, wherein said second sequence is a subsequence of said first sequence and is at least 14, preferably at least 17 or 20, more preferably at least 25, nucleotides in length; (3) a third sequence in which at least one nucleotide of said first or second sequences is replaced by a different nucleotide; or (4) a fourth sequence complementary to any of said first, second or third sequences; with the proviso that (i) if said molecule is an RNA molecule, U replaces T in said sequence of said molecule, (ii) said third sequence is at least 90%, preferably at least 95%, identical to said first or second sequence, and (iii) said second sequence is not nucleotides 347–667, 1564–1696, or 2110–2386 of SEQ. ID NO:1. Also included as DNA of the invention is the corresponding genomic sequence, including introns. These non-coding sequences include terminator and polyadenylation sequences, regulatory protein binding sequences, transcriptional sequences, and the like. Molecules containing the full length AC133 cDNA sequences are useful as sources of subsequences or as starting materials for the preparation of the AC133 molecule itself.

A "subsequence" is a group of consecutive nucleotides from the cDNA sequence. Any of these sequences can be used in the identification of the presence (or absence) of the AC133 gene or of the expression of mRNA encoding the AC133 antigen. Such subsequences can be prepared by chemical synthesis from starting nucleotides (as in an automated gene synthesizer) or by biochemical manipulation of the full-length sequences (e.g., using restriction endonucleases to prepare fragments, optionally followed by (1) cleavage of terminal nucleotides and exonucleases and/or (2) size sorting and/or affinity capture to select the desired sequence). Any subsequence of the AC133 sequence described in SEQ ID No.: 1 of sufficient length to be unique among the other nucleic acids present under the conditions being used is useful as one of the two primers used in a polymerase chain reaction (PCR) amplification of all or part of the genomic AC133 gene. The length of a subsequence necessary to hybridize uniquely with the desired target sequence will vary with the particular method being used, and selection of the length is within the ordinary skill of those who carry out routine identification of genetic material. A preferred subsequence is at least 15 nt in length, more preferably at least 18 nt, even more preferably at least 19, 20, 21, 25, or 30 nt in length up to the full length of the nucleotide sequence shown as SEQ. ID NO:1, preferably less than 200 nt in length if used as a hybridization probe or less than 50 nt in length if used as a PCR primer.

Three subsequences within the coding region of SEQ. ID NO:1 were previously recorded in Genbank as EST's of unknown function. Accordingly, these Genbank subsequences, nucleotides 347–667, 1564–1696, and 2010–2386, are not claimed as subsequences of the invention. Additionally, there are a number of EST's in Genbank from the 3' untranslated region of SEQ. ID NO:1, also of unknown function, specifically in the regions covered by nucleotides 2684–3332 and 3408–3804. Subsequences from these two regions are not claimed as part of the present invention. Longer subsequences of the entire sequence shown as SEQ. ID NO:1 that contain one or more of the Genbank sequences, as well as subsequences of any length that include part of one or more Genbank sequence but also contain newly identified nucleotides set forth in SEQ. ID NO:1, are considered to be part of the present invention.

The nucleic acid compositions of the subject invention can be genomic or cDNA sequences encoding all or a part of the subject protein. Fragments can be obtained of the cDNA or genomic sequence by chemically synthesizing oligonucleotides in accordance with conventional methods, such as by restriction enzyme digestion or by PCR amplification. For the most part, fragments will be of at least 12 nt, more usually at least 18 nt, or one of the other lengths described above. Preferred fragments will include a functional epitope. The sequence providing for a functional epitope can be determined by expression of the sequence, and assaying for reactivity of the expression product with specific antibodies by conventional immunoassay.

Exemplary amino acid and DNA sequences of the invention are set forth in SEQ ID No.: 1 and 2 below. Standard abbreviations for nucleotides and amino acids are used in this specification. Polypeptides derived from the natural AC133 antigen are particularly preferred embodiments of the invention, although variations based on the specific sequences of these polypeptides are also parts of the present invention. In its broader aspects the invention (as it pertains to polypeptides per se) includes any polypeptide selected from the group consisting of (1) a first amino acid sequence of AC133 as set forth in SEQ ID NO: 2; (2) a second amino acid sequence wherein the second sequence is a subsequence of the first sequences and is at least 6, preferably 8, more preferably 10, amino acids in length; or (3) a third sequence in which at least one amino acid of the first or second sequences is replaced by a different amino acid, with the proviso that the amino acid replacement is a replacement of one acidic residue for another, one basic residue for another, one non-polar residue for another, one uncharged polar residue for another, or one aromatic residue for another, with the proviso that the third sequence is at least 90%, preferably 95%, identical to the first or second sequence.

Two amino acid sequences are homologous if there is a partial or complete identity between their sequences. For example, 85% homology means that 85% of the amino acids are identical when the two sequences are aligned for maximum matching. Gaps (in either of the two sequences being matched) are allowed in maximizing matching. Gaps of 5 or less are preferred with 2 or less being more preferred. Alternatively and preferably, two protein sequences (or polypeptide sequences derived from them of at least 30 amino acids in length) are homologous as this term is used herein, if they have an alignment score of more than 5 (in standard deviation units) using the program align with the mutation data matrix and a gap penalty of 6 or greater (Dayhoff, M. O., in Atlas of Protein Sequence and Structure, 1972, vol. 5, National Biomedical Research Foundation, pp. 101–110, and supplement 2 to this volume, pp. 1–10). The two sequences or parts thereof are more preferably homologous if their amino acids are greater than or equal to 50% identical when optimally aligned using the align program.

Minor amino acid variations from the natural amino acid sequence sets forth in SEQ ID No.: 2 are contemplated; in particular, conservative amino acid replacements are contemplated. Conservative replacements of those that take place within a family of amino acids that are related in their side chains. Genetically encoded amino acids are generally divided into four families: (1) acidic, aspartate, glutamate; (2) basic: lysine, arginine, histidine; (3) non-polar: alanine, valine, leucine, isoleucine, proline, phenylalanine, methionine, tryptophan; and (4) uncharged polar: glycine, asparagine, glutamine, cysteine, serine, threonine, tyrosine. Phenylalanine, tryptophan and tyrosine are sometimes classified jointly as aromatic amino acids. For example, it is reasonable to expect that an isolated replacement of a leucine with an isoleucine or valine, an aspartate with a glutamate, a threonine with a serine, or a similar replacement of an amino acid with a structurally related amino acid will not have a major effect on the binding properties of the resulting molecule, especially if the replacement does not involve an amino acid as a binding site involved in the interaction of AC133 or its derivatives with a reagent that binds specifically to AC133. Whether an amino acid change results in a functional peptide can readily be determined by assaying the specific binding properties of the polypeptide derivative.

As shown in FIG. 13, there are a number of regions having different functions in the peptide structure of AC133. These regions can be described (beginning with the amino terminus) as an extracellular N-terminus, a first transmembrane region, a first cytoplasmic loop, a second transmembrane region, a first extracellular loop, a third transmembrane region, a second cytoplasmic loop, a fourth transmembrane region, a second extracellular loop, a fifth transmembrane, and a cytoplasmic C-terminus. Approximate sizes of the regions are shown in FIG. 13, with best estimates of the amino acids present in the different regions being as follows: extracellular N-terminus, aa 20–107; first transmembrane region, aa 107–126; first cytoplasmic loop, aa 127–157; second transmembrane region, aa 158–179; first extracellular loop, aa 180–435; third transmembrane region, aa 436–454; second cytoplasmic loop, aa 455–480; fourth transmembrane region, aa 481–503; second extracellular loop, aa 504–792; fifth transmembrane, aa 793–816; and cytoplasmic C-terminus, aa 817–865. There appears to be a cleavable signal sequence (aa 1–19) at the amino terminus of the encoded peptide; this sequence is not included as part of the regions shown in FIG. 13 but will be present in synthetically produced AC133 peptides.

Also shown in FIG. 13 are the approximate locations of short peptide segments (P1–P4) that were identified to verify the structure of the AC133 antigen and of glycosylation sites (indicated by a "Y" at the point of attachment). FIG. 12 also shows the glycosylation sites (which are boxed in the amino acid sequence) and transmembrane regions (which are underlined). Two glycosylation sites overlap (NNTS, which consists of an overlapping NNT and NTS) and are shown by a larger box with dashed lines indicating the individual consensus glycosylation sites.

The DNA sequences can be obtained in substantial purity and can be obtained as an isolated molecule other than a sequence of an intact chromosome. Usually, the DNA will be obtained substantially free of other nucleic acid compounds, generally being at least about 50%, usually at least about 90% pure and are typically "recombinant", i.e., flanked by one or more nucleotides with which they are not normally associated with on a natural chromosome.

The DNA sequences are used in a variety of ways. They can be used as probes for identifying related surface proteins in the same or other species. The DNA can also be used to identify cells or organs that are expressing the subject genes. Techniques in which one probes cells for the presence of particular nucleotide sequences, particularly as DNA, mRNA or cDNA, are well-established in the literature and do not require elaboration here. Conveniently, mRNA can be isolated free of DNA, and by using reverse transcriptase and PCR with specific primers, the subject cDNAs of interest of can be expanded, separated on gel electrophoresis and then probed using Southern blotting or sequencing. Other techniques can also find use.

Homologous sequences are those with substantial sequence similarity to AC133 antigen sequences included within the subject invention, i.e., at least 80%, preferably at least 90%, more preferably at least 95%, sequence identity with the nucleotide sequence of the subject DNA sequence. Sequence similarity is calculated based on a reference sequence, which can be a subset of a larger sequence, such as a conserved motif, coding region, or flanking region. A reference sequence will usually be at least about 18 nt long, more usually at least about 30 nt long, and can extend to the complete sequence that is being compared. Such homologous nucleic acid sequences will be detected by hybridization under low stringency conditions, for example, at 50° C. and 10×SSC (0.9 M NaCl/0.09 M sodium citrate) and remain bound when subject to washing at 55° C. with 1×SSC.

For expression, the DNA sequences can be inserted into an appropriate expression vector, where the native transcription initiation region can be employed or an exogenous transcriptional initiation region. The promoter can be introduced by recombinant methods in vitro, or as the result of homologous integration of the sequence into a chromosome. A wide variety of transcriptional initiation regions are known for a wide variety of expression hosts, where the expression hosts can involve prokaryotes or eukaryotes, particularly *E. coli, B. subtilis,* mammalian cells, such as CHO cells, COS cells, monkey kidney cells, lymphoid cells, particularly human cell lines, and the like. Generally a selectable marker operative in the expression host will be present. The promoter can be operably linked to the coding sequence of the genes of interest so as to produce a translatable mRNA transcript. Expression vectors have convenient restriction sites located near the promoter sequence so as to provide for the insertion of nucleic acid sequences encoding heterologous proteins. The promoters in suitable expression vectors can be either constitutive or inducible. Expression vectors for the production of fusion proteins, where the exogenous fusion peptide provides additional functionality, such as increased protein synthesis, stability, reactivity with defined antisera, or an enzyme marker, e.g., β-galactosidase, are of particular interest.

Expression cassettes can be prepared comprising the transcription initiation region, which can be constitutive or inducible, with or without an enhancer sequence, including the endogenous or heterologous enhancer sequence, the AC133 gene or fragment thereof, and a transcriptional termination region, optionally having a signal for attachment of a poly A sequence. The gene can be genomic, including the native introns, or cDNA gene, or portion thereof. Of particular interest is the use of sequences which allow for the expression of functional epitopes, usually at least about 24 nucleotides in length, more usually at least about 48 nucleotides in length, and up to the complete open reading frame of the gene.

After introduction of the DNA, the cells containing the construct can be selected by means of a selectable marker, the cells expanded and then used for expression. Where secretion is desired, a signal peptide can be joined to the sequence encoding the subject proteins or fragments thereof, whereby the protein will be expressed, translocated through the cell membrane, and processed to remove the signal peptide.

The expression cassettes can be introduced into a variety of vectors, where the vectors will normally be characterized by the ability to provide selection of cells comprising the expression vectors. The vectors can provide for extrachromosomal maintenance, particularly as plasmids in bacteria or viruses in eukaryotic cells, or for integration, particularly in mammalian cells. Where extrachromosomal maintenance is desired, an origin sequence will be provided for the replication of the plasmid, which can be a low- or high-copy plasmid. A wide variety of markers are available for selection, particularly those which protect against toxins, more particularly against antibiotics. The particular marker which is chosen will be selected in accordance with the nature of the host, where in some cases, complementation can be employed with auxotrophic hosts, e.g., yeast. Introduction of the DNA construct can be by any convenient means, e.g., calcium-precipitated DNA, electroporation, fusion, transfection, or infection with viral vectors.

The following examples are offered by way of illustration and not by way of limitation.

EXAMPLES

Generation of the AC133 Monoclonal Antibody by Contralateral Immunization. Five New Zealand Black (NZB) mice were inoculated a total of seven times over a twenty day period, via the footpad route, with purified CD34 positive human progenitor cells, which had been pre-incubated with phytohemagglutinin (PHA) (Gibco/BRL).

Mice were pre-immunized on Day-3 in the left hand footpad with cells that express many immunodominant but irrelevant antigens. In this case peripheral blood mononuclear cells (PBMC) were used as an irrelevant cell, as they express many antigens such as Class I HLA antigens, HLA-DR, CD15, CD26, CD29, CD31, CD36, CD44, CD45, CD58, etc., which are also expressed on hematopoietic stem cells. On day 0 PBMC are reinjected into the left footpad, and purified stem cells are injected into the right hand footpad. PBMC and purified stem cells are pre-incubated with PHA for ten minutes and washed with PBS prior to injection. Progenitor cells were isolated from a leukaphoresis pack of a cytokine mobilized donor using immunomagnetic beads. This treatment provides non-specific adjuvant effects, and obviates the need adjuvants such as Freund's. Mice are given a total of 5–8 such injections at three days intervals.

On day 21, one day after the last injection, the mouse right hand popliteal lymph nodes were removed. A lymphocyte suspension was prepared, and the cells fused to SP2/0 Ag14 myeloma cells using a modification of the method originally described by Kohler and Milstein (1975) *Nature* 256:495–497. Cells were plated on 96 well plates in DMEM+20% fetal calf serum, with $10^{-4}$ M hypoxanthine and 2 μg/ml azaserine (Buck et al. (1984) in *Monoclonal Antibodies and Functional Cell Lines* Kennet et al. eds., Plenum Press, New York pp.275–309). On day 10, visible hybridoma colonies were apparent. Supernatants (s/n) from hybridoma containing wells were screened for binding to a fetal liver cell preparation containing up to 15% CD34+ cells, using a 2 color flow cytometry assay. Binding of mouse Ig containing s/n to the test cells was traced with rat anti-mouse Ig-conjugated to phycoerythrin (IgPE) and counterstained with a known mouse anti-CD34 antibody (AC101) conjugate. FIG. 1 shows the results from this two color FACS analysis using AC133 supernatant. AC133 is shown to stain only the bright CD34 positive cells in the fetal liver preparation. AC133 hybridoma cells were shown to secrete an IgG1/kappa antibody. The cells were expanded in culture and stocks frozen in liquid nitrogen. AC133 cells were subcloned by limiting dilution analysis and a series of positively secreting subclones were also frozen in liquid nitrogen.

Antibody purification and conjugation. AC133 cells were initially grown as an ascites tumor in nude mice, with collection of antibody-rich ascites fluid. More recently AC133 cells have been grown to very high density in a hollow fiber culture device (Cellmax QUAD artificial capillary system, Cellco Inc., Germantown, Md.). Pure IgG antibody was prepared from hollow fiber cultures or from ascites fluid by Protein A chromatography. Pure antibody was stored in 0.01M phosphate buffered saline (PBS) with 0.01% sodium azide at 4° C. This pure antibody stock was used to prepare fluorescein isothiocyanate (FITC) (Wofsy et al. (1980)in *Selected Methods in Cellular Immunology,* Mishell and Shiigi eds., W. H. Freeman and Co., San Francisco. pp.294–295), phycoerythrin (PE) (Hardy (1986) in *Handbook of Experimental Immunology,* Weir et al., eds. Blackwell Scientific Press, Oxford. p.31), or magnetic bead conjugates, according to standard protocols.

AC133 expression on normal tissues and cell lines. Using standard FACS staining procedures, there was no detectable staining of peripheral blood mononuclear cells, granulocytes or platelets, or human umbilical vein endothelial cells with AC133 antibody. Examination of a panel of human cell lines by FACS analysis (data shown in Table 1) showed that only three cell lines tested, the retinoblastoma cell lines Y79.1 and WERI-Rb-1 and the teratocarcinoma cell line NT-2, expresses detectable levels of AC133 antigen.

TABLE 1

AC133 Expression on Human Cell Lines

| Cell Line | Cell Type | AC133 |
|---|---|---|
| 8402 | T cell line (CD34+) | – |
| 8866 | B-LCL | – |
| AZ676 | breast carcinosarcoma | – |
| BJAB | N. American Burkitts' Lymphoma | – |
| BT474 | breast tumor | – |
| BT549 | breast tumor | – |
| BT20 | breast tumor | – |
| CaCL74-36 | melanoma | – |
| Daudi | B-LCL- | – |
| Du4475 | breast tumor (CD34+) | – |
| HBL92.1.7 | erythroleukemia | – |
| HL-60 | promyelocytic leukemia | – |
| HPB-ALL | acute lymphocytic leukemia | – |
| HS-R | myeloma (EBV+) | – |
| HT1080 | fibrosarcoma | – |
| HT29 | colon adenocarcinoma | – |
| IM-9 | B-LCL | – |
| JM | T cell line | – |
| Jurkat | T cell line | – |
| KG1a | acute myelogenous leukemia (CD34+) | – |
| KG1 | acute myelogenous leukemia (CD34+) | – |
| KG1a.5 | acute myelogenous leukemia (CD34+) | – |
| K562 | erythroleukemia | – |
| MOLT-4 | T cell line | – |
| MCF-7 | breast tumor | – |
| Raji | B-LCL | – |
| RPMI 8226 | myeloma | – |
| SK HEP-1 | hepatoma | – |
| U937 | histiocytic lymphoma | – |
| WERI-Rb-1 | retinoblastoma | + |
| Y79.1 | retinoblastoma | + |
| NT-2 | teratocarcinoma | + |

Figure 2:
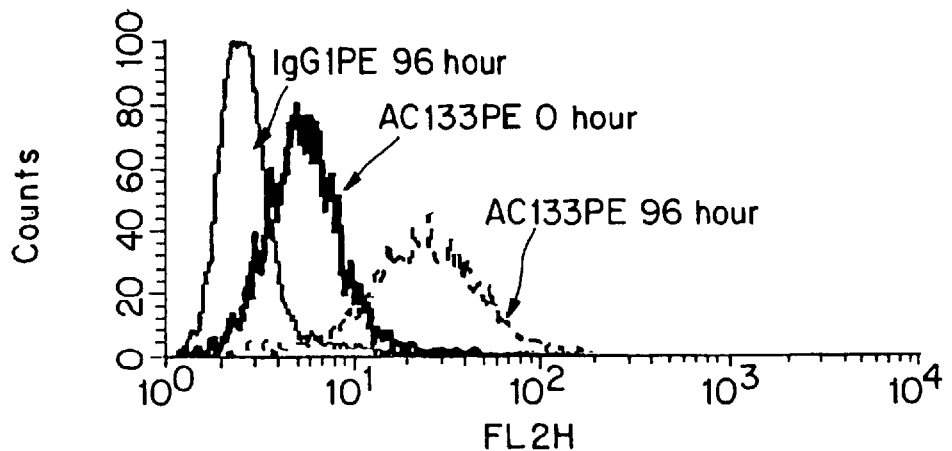
FIG. 2 is a graph showing FACS analysis of AC133 antigen expression on phorbol myristate acetate (PMA) activated Y79.1 cells.
Figure 3:
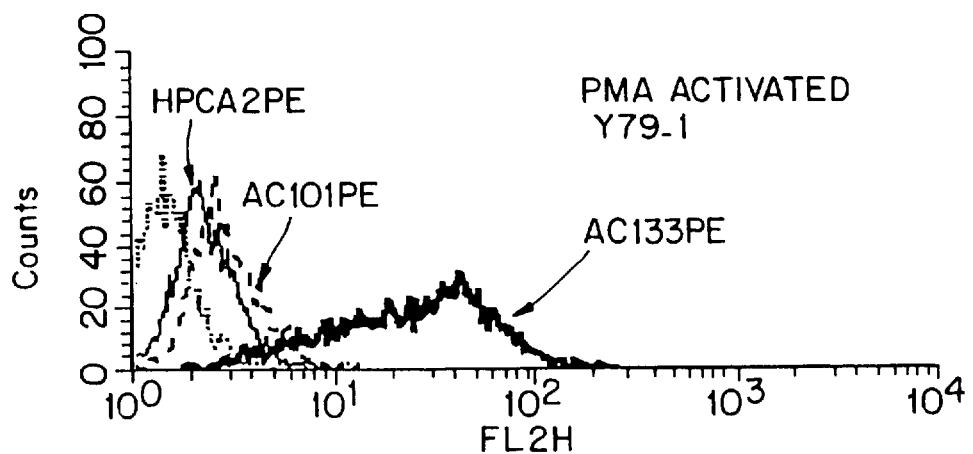
FIG. 3 is a graph showing FACS analysis of AC133 antigen and CD34 expression on PMA activated Y79.1 cells.

Activation of Y79.1 cells with PMA was found to increase the expression of AC133 antigen (shown in FIG. 2). However, PMA activation of several other cell lines, or PHA activation of human PBMC was unable to induce the expression of AC133 antigen (data are shown in Table 2). AC133 antigen expression was not detectable on any of the CD34+ cell lines tested. This finding, along with the lack of CD34 expression on the Y79.1 cell line (shown in FIG. 3), excludes the possibility that AC133 is directed to the CD34 antigen. AC133 antigen expression is limited to primitive stem and progenitor cells, unlike the CD34 antigen, which is also expressed on endothelium and fibroblasts (Krause et al. (1996) *Blood* 87:1–13).

The AC133 antigen is expressed on the CD34$^{bright}$ population of human progenitor cells isolated from fetal and adult bone marrow, fetal liver, cord blood, leukaphoresis (LP)

packs and LP packs from cytokine mobilized donors. Typically it stains 30–50% of all CD34+ cells in these populations.

TABLE 2

Activation of Cell Lines

Addition of PMA at 1 ng/ml for:

|         | 0 hr  | 24 hr | 48 hr | 72 hr | 96 hr | 144 hr |
|---------|-------|-------|-------|-------|-------|--------|
| Y79.1   | dim+  | +     | +     | +     | +     | +      |
| KG1a    | −     | −     | −     | −     | −     | N/A    |
| K562    | −     | −     | −     | −     | −     | N/A    |
| HEL 92.1.7 | −  | −     | −     | −     | N/A   | N/A    |
| Jurkat  | −     | −     | −     | N/A   | N/A   | N/A    |
| 8402    | −     | N/A   | N/A   | −     | N/A   | N/A    |

Addition of PWM at 10 µg/mL for:

|       | 0 hr | 24 hr | 48 hr |
|-------|------|-------|-------|
| Y79.1 | dim+ | +     | +     |
| KG1a  | −    | −     | −     |

Figure 4A:
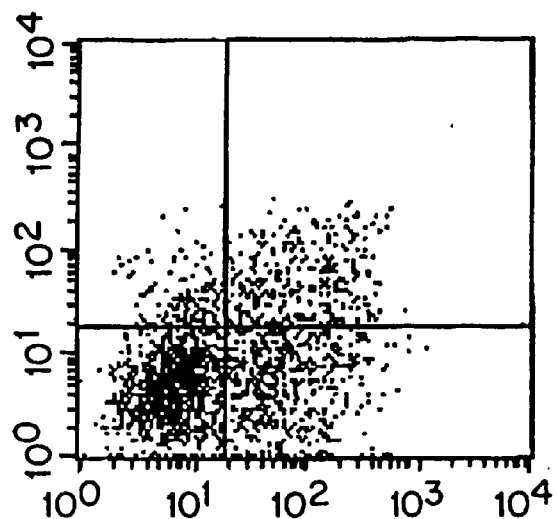
FIGS. 4A and 4B show dot-plots from 3 color FACS analysis of the antibodies AC133, CD38 and HLA-DR on fetal liver cells. The x axis in FIG. 4A represents HLA-DR-FITC, and the y axis represents cell staining with AC133-PE. The x axis in FIG. 4B represents CD38-FITC, and the y axis represents cell staining with AC133-PE.
Figure 4B:
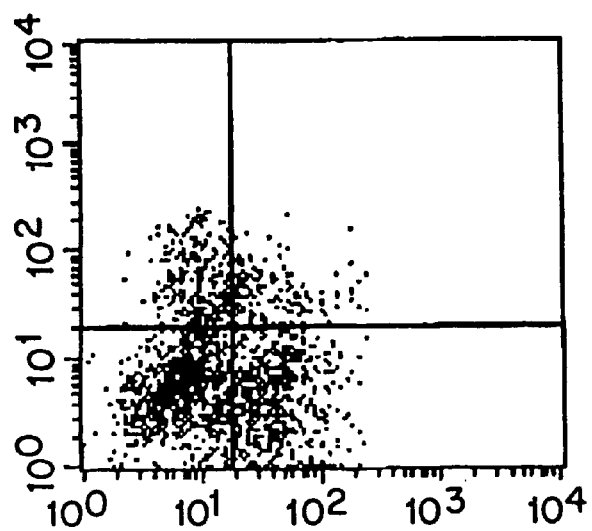
Figure 5A:
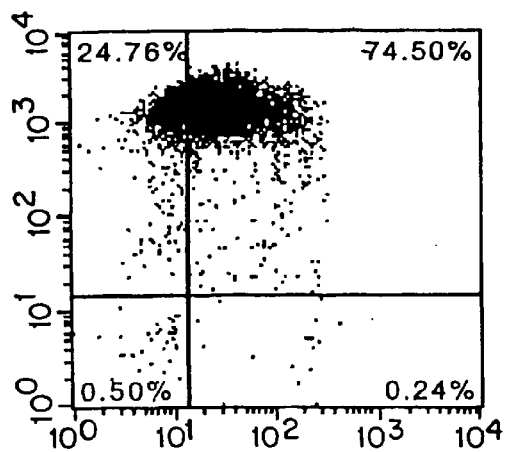
FIGS. 5A, 5B, 5C and 5D show dot-plots from FACS analysis of the antibodies CD38, HLA-DR, CD90 and CD117 on AC133 positive cells purified from fetal liver.
Figure 5B:
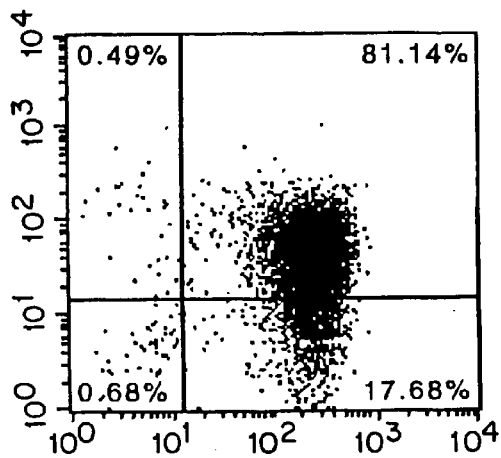
Figure 5C:
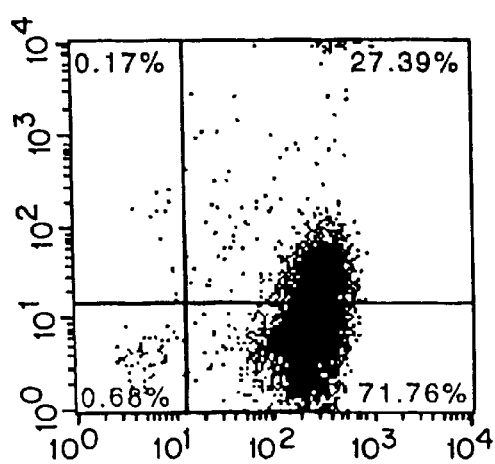
Figure 5D:
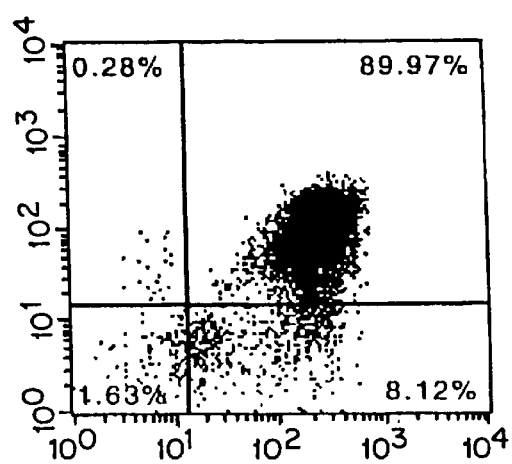

Phenotyping of AC133 positive cells. Phenotyping of AC133 and CD34 double positive cells was accomplished using 2 and 3 color FACS analysis, employing a panel of conjugated antibodies directed to cell surface structures known to be expressed on progenitor cells. Fetal liver, fetal and adult bone marrow, cord blood and peripheral blood were all used to determine the precise phenotype of AC133 positive cells. AC133 cells found in all of these tissues are $CD34^{bright}$, $CD38^{-/+}$ and $HLA-DR^{-/+}$. The data are shown in FIG. 4. The CD90 (Thy1)+ and CD117 (c-kit)+ stem cell populations are included within the AC133 positive population, as shown in FIG. 5. In a series of experiments performed with AC133 immunomagnetically purified fetal liver cells, CD38-FITC conjugated antibody stained 74.5% of the AC133 purified cells, while 24.8% were CD38 negative. As expected, HLA-DR stained the majority of the cells (81.14%). CD90 is shown to stain 27.4% of the test cells, while CD117 stained 90%. It is generally believed that primitive (repopulating) hematopoietic stem cells have the phenotype of $CD34^{bright}$, $CD38^{dim/neg}$, $HLA-DR^+$, $CD117^{dim}$ and CD90+. Thus, the AC133 antibody recognizes a phenotypically important population of human hematopoietic progenitor cells.

Immunoprecipitation of the AC133 antigen. Immunoprecipiation experiments showed that the AC133 antigen has a molecular weight of 120 kD. Biotin (Pierce) labeled, activated Y79.1 and Weri-RB-1 cells were solubilized with lysis buffer: 2.5% Brij (Sigma), 25 mM Tris-HCl, pH8.0, 125 mM NaCl, 2.5 mM EDTA, 2.2 µg/ml Aprotinin (Sigma) and 1 mM PMSF (Sigma). The lysates were incubated with AC133 and control antibodies after preclearing. Immunocomplexes were collected on *Staphylococcus aureus* cells (CalBiochem) and heated for five minutes at 95° C. in SDS-PAGE sample buffer with 1% 2-mercaptoethanol. Immunoprecipitates were resolved by SDS-PAGE and transferred to nitrocellulose membranes (Novex). Visualization was accomplished using streptavidin linked to horseradish peroxidase (HRP) (Amersham) and the Supersignal CL-HRP substrate system (Pierce). CD49d, CD71 and CD98 were used as controls, and their expected bands of 133 kD, 92 kD and 80/40 kD were observed in the corresponding lanes. The immunoprecipitation with AC133 showed a distinct band corresponding to a molecular weight of 120 kD. This band was absent in the samples that were immunoprecipitated with the anti-CD34 antibodies AC101, HPCA1 and HPCA2, indicating that CD34 is not expressed in the Y79.1 cell line. This is consistent with the FACS data.

Figure 6:
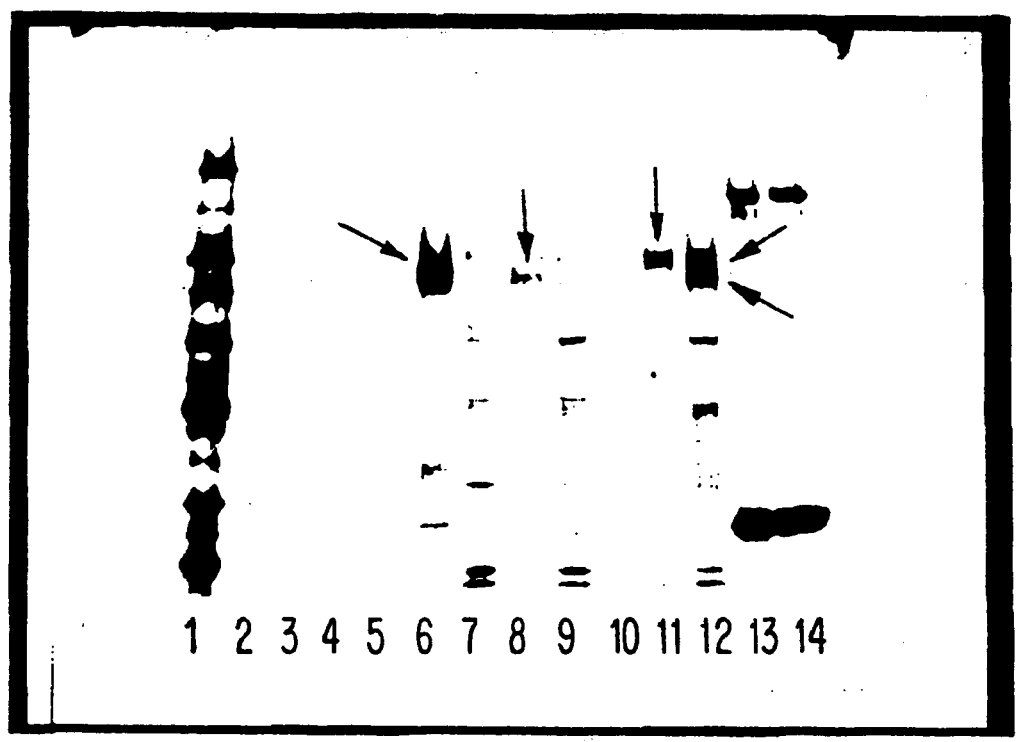
FIG. 6 is a gel showing the results of an immunoprecipitation with AC133 antibody and the cell lines KG1a and Y79.1. The lanes are as follows: 1) molecular weight markers; 2) a 1:5 dilution of unprecipitated KG1a lysate; 3) a 1:50 dilution of unprecipitated Y79.1 lysate; 4) KG1a lysate precipitated with AC101 antibody (CD34); 5) Y79.1 lysate precipitated with AC101 antibody; 6) KG1a lysate precipitated with HPCA2 antibody (CD34); 7) Y79.1 lysate precipitated with HPCA2 antibody; 8) KG1a lysate precipitated with 16D11 antibody (CD34); 9) Y79.1 lysate precipitated with 16D11 antibody; 10) KG1a lysate precipitated with AC133 antibody; 11) Y79.1 lysate precipitated with AC133 antibody; 12) mixed kG1a and Y79.1 lysate precipitated with a mixture of AC133 and HPCA2 antibodies; 13) KG1a lysate precipitated with 8A3 (anti-CD109) antibody; 14) KG1a lysate precipitated with 15G5 (anti-CD109) antibody.

The data from a further experiment is shown in FIG. 6, where biotin labeled Y79.1, as well as KG1a cells, confirmed the AC133 molecular weight data by comparing CD34 and AC133 precipitates on the same gel. In this experiment, CD34 and Y79.1 antigens were precipitated from biotinylated KG1a (CD34+) and Y79.1 lysates in adjacent lanes. The results clearly demonstrate that 1) each antibody precipitates its own distinct antigen, and 2) that the molecular weight of these two antigens is distinctly different, being 110 and 127 kD, respectively. In control lanes 6 and 8, HPCA2 and 16D11 (anti-CD34) precipitate a band of 110 kD from KG1a lysate, but do not precipitate anything from Y79.1 lysate (lanes 7 and 9). AC133 precipitates a 120 kD protein from the Y79.1 lysate (lane 10), but nothing from the KG1a lysate in lane 11. In lane 12, KG1a and Y79.1 lysates were mixed, and AC133 Ag and CD34 were co-precipitated. The results show that the two antigens are of different molecular weights.

AG133 magnetic bead conjugation. Purified AC133 antibody was conjugated to magnetic amino-dextran beads using a standard protocol for 4-(N-maleimidomethyl)-cyclohexane-1-carboxylic acid N-hydroxysuccinimide ester (SMCC). AC133 antibody was added to SMCC activated beads at 5 µg per $OD_{450}$ unit, and incubated at room temperature for two hours. The reaction was stopped by the addition of β-mercaptoethanol and NEM. The conjugate was purified over two columns in the presence of a magnetic field, and eluted. The concentration was adjusted to $OD_{450}=$ 10, and OPG was added for stabilization. The conjugate in PBS and 0.1% sodium azide was filtered through a 0.2 µm filter, and stored at 4° C.

Figure 8:
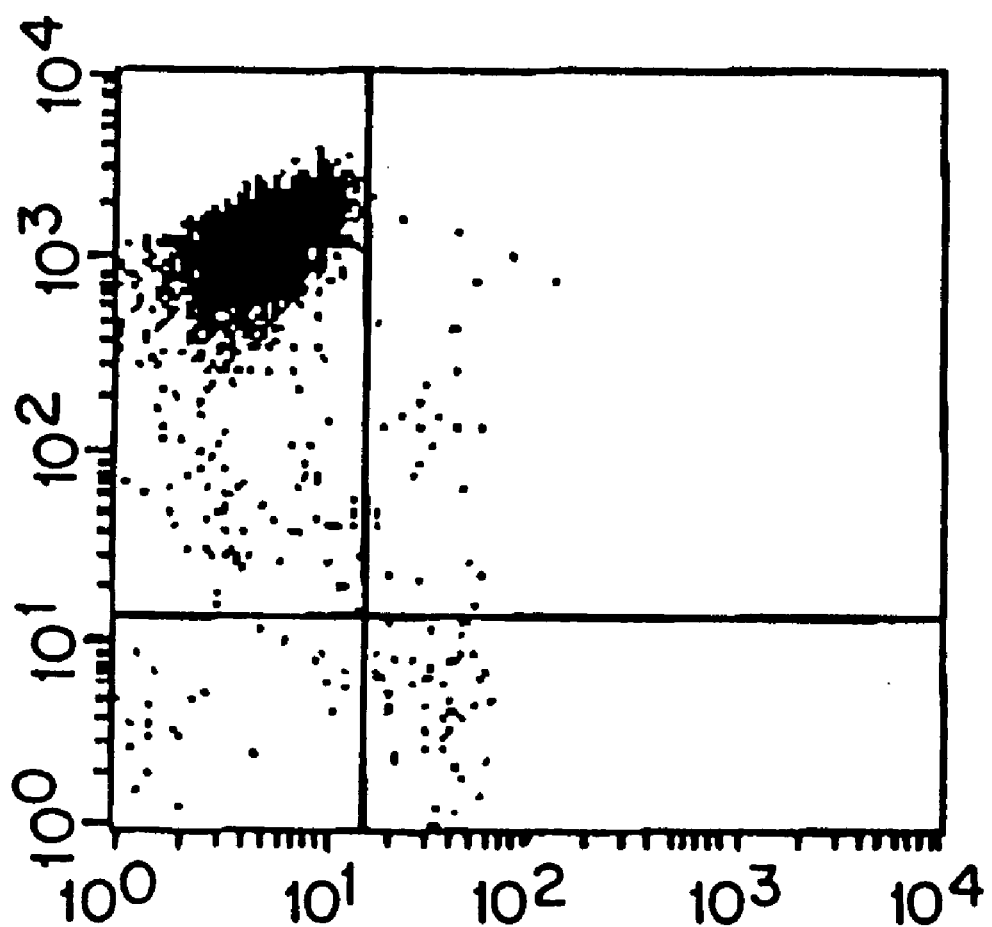
FIG. 8 is a dot-plot showing FACS analysis of HPCA2-PE (y axis) staining of AC133 magnetically purified fetal liver cells. The x axis represents staining with a glycophorin A-FITC conjugate.
Figure 9A:
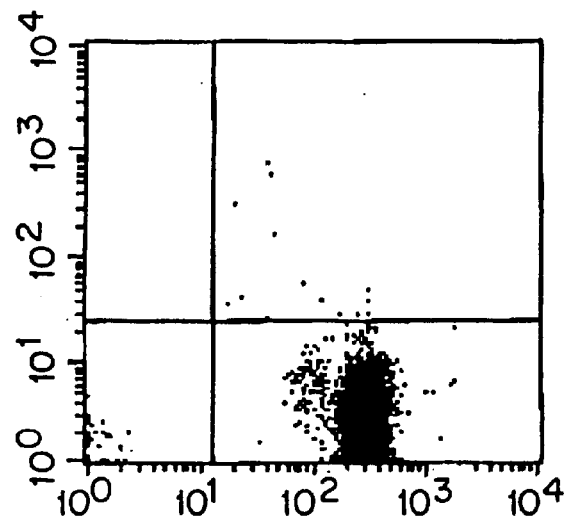
FIGS. 9A and 9B are dot plots showing FACS analysis of HCPA2 staining of buffy coat peripheral blood mononuclear cells before and after AC133 magnetic separation. The y axis shows staining with HCPA2-PE, the x axis shows staining with anti-CD45 and anti-CD15-FITC conjugated antibodies.
Figure 9B:
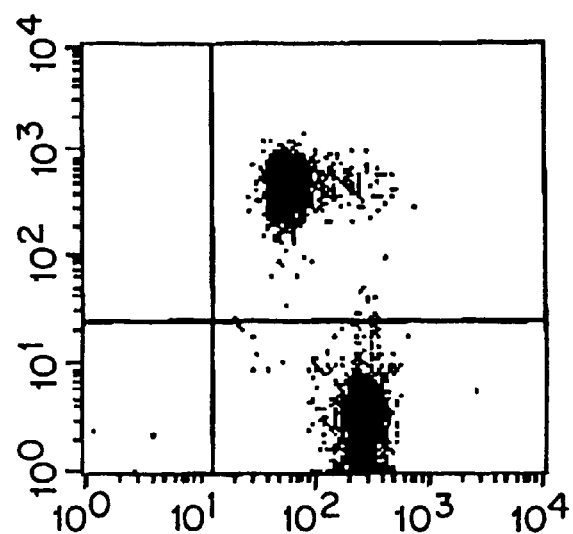

Separation of human hematopoietic progenitor cells with AC133 magnetic bead conjugate. AC133 direct magnetic bead conjugates were prepared and tested on buffy coat PBMCs, fetal liver WCl, fetal bone marrow and adult bone marrow. FIG. 8 shows the FACS dot plot of fetal liver cells purified with AC133 bead conjugate using the miniMACS system and stained with glycophorin A-FITC and HCPA2-PE. The starting material contained 7.4% CD34+ cells, following AC133 purification, greater than 90% of AC133 purified cells were bright CD34+. FIG. 9 shows that AC133 magnetic conjugate was also very effective in enriching CD34+ cells from a buffy coat which contained about 0.26% CD34+ cells. The final purified population was 64% positive for CD34, as shown by HPCA2-PE staining. This ability to separate cells in a magnetic purification system enables further study of the functional and phenotypic properties of AC133.

Figure 10:
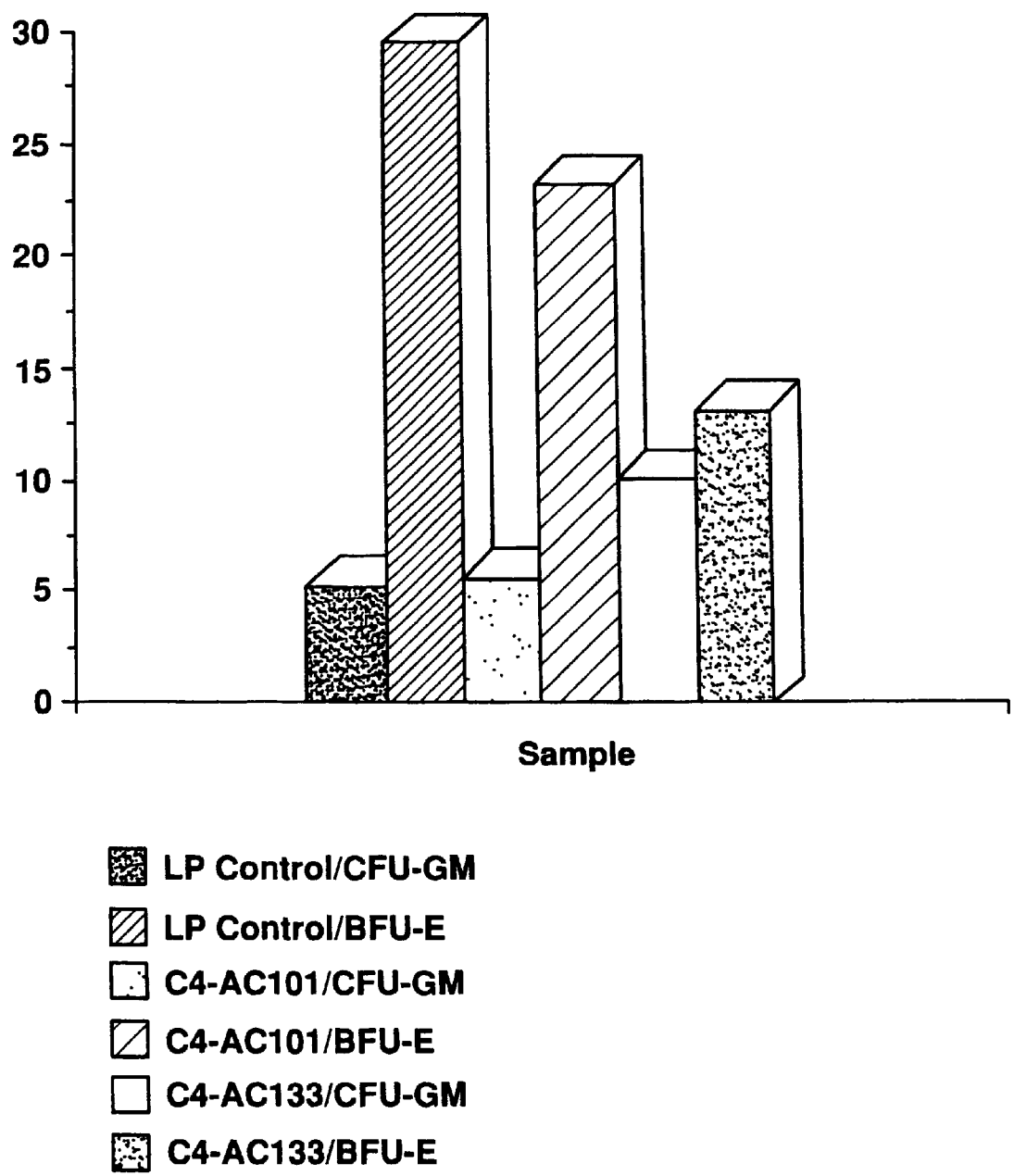
FIG. 10 is a bar graph showing the cloning efficiency of AC133 and AC101 purified cells in a clonogenicity assay.

Clonogenic potential of AC133 positive cells. AC133 magnetic beads selected cells purified from leukaphoresis packs were tested in clonogenicity assays using a commercially available kit (Stem Cell Technologies, Vancouver, B.C.). By providing a controlled growth environment utilizing recombinant human growth factors this culture assay identifies the major colony forming units (CFU) within a CD34 positive cell population. It provides information on the composition of progenitor cell populations, with respect to the relative percentages of cells committed to a particular lineage specific differentiation. Typically in peripheral blood derived CD34+ cell populations BFU-e (burst forming units-erythroid), and CFU-GM (colony forming units-granulocyte macrophage) are the predominant colonies recognized, being present at a 3:1 ratio. FIG. 10 shows the results from a typical clonogenicity experiment comparing AC133 and CD34 purified cells obtained from a split leukaphresis pack. Colonies obtained with unfractionated control cells are typically predominantly BFU-E (29.34%), with a smaller number of CFU-GM (5.14%). CD34 purified cells show a similar distribution with 23.3% BFU-E, and 5.58% CFU-GM. In contrast, AC133 purified cells show a different pattern, with 13.1% BFU-E and 10.2% CFU-GM. Calculations show that 58% of CFU-GM were recovered in the AC133 purified fraction, while only 13% of BFUEs were recovered.

Figure 11:
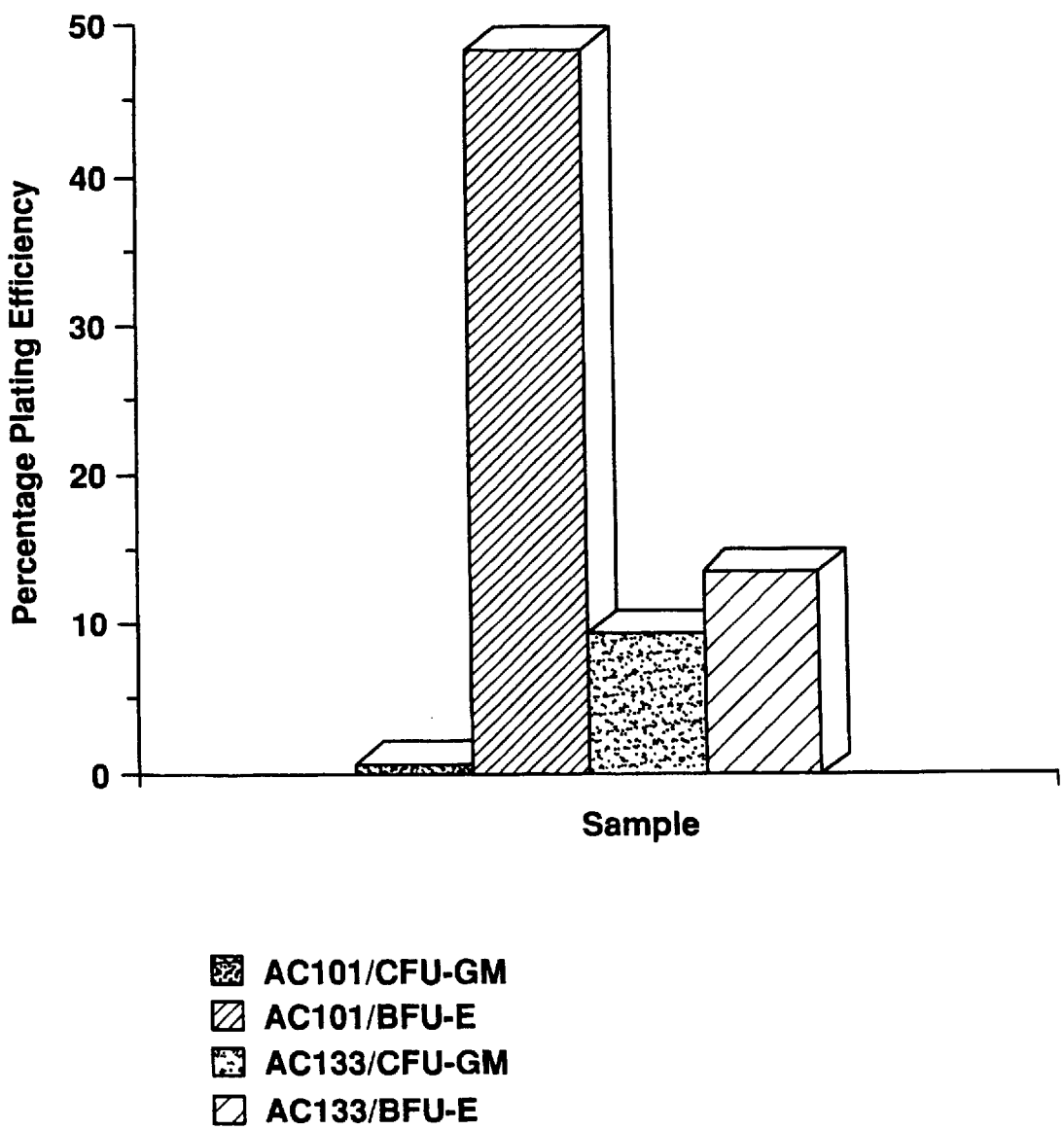
FIG. 11 is a bar graph showing the plating efficiency of AC133 purified cells and AC133 negative, CD34 positive cells.

FIG. 11 shows the results from a similar clonogenicity assay obtained following AC133 immunomagnetic purification. In this experiment, AC133 cells were positively selected, and then CD34 positive cells were positively selected from the AC133 negative flow-through. This design allowed the direct comparison of AC133$^+$ cells with CD34$^+$ but AC133$^-$ cells from the same donor. The results indicate that 93.8% of the CFU-GM progenitors were recovered in the AC133 positive fraction, the remaining 6.2% being recovered from the CD34+/AC133$^-$ fraction. Conversely, the CD34$^+$ AC133$^-$ fraction contained 78.0% of the BFU-e progenitors, while the remaining 22.0% were contained in the AC133$^+$ fraction.

The above experimental results rule out the possibility that an anti-AC133 antibody is an antibody to Fc receptors, or that an anti-AC133 antibody binds to stem cells via Fc receptor uptake. Further experiments rule out the possibility that AC133 antibody staining is due to free PE. AC133 antibody does not behave like an antibody to RTK, a receptor tyrosine kinase, TIE, a tyrosine kinase that contains immunoglobulin-like domains and growth factor homology domains and which is expressed in vascular endothelial cells and hematopoietic cells. AC133 antibody also does not behave like an antibody to P-glycoprotein, a 170 kD multidrug resistance product which is also expressed in hematopoietic cells.

We have shown that AC133 antibody recognizes an antigen expressed only on bright CD34+ cells in bone marrow, fetal liver and peripheral blood. This antibody and its antigen do not match the molecular weight or distribution of any known CD antigen. Apart from stem cells, AC133 antibody has been shown to react with a human retinoblastoma cell line that is negative for CD34 expression. AC133 antigen is, in addition, not expressed on a number of CD34+ cell lines.

It is evident from the above results that the subject invention provides for a novel antigen found on primitive stem cells and a subset of hematopoietic progenitor cells, as well as antibodies that specifically bind to the antigen. Expression of the antigen is highly tissue specific. It is only detected on a subset of hematopoietic progenitor cells, and is present on substantially all cells that are active in the CFU-GM assay. This highly specific distribution of AC133 antigen makes it exceptionally useful as a reagent for isolating and characterizing human hematopoietic progenitor and stem cells.

Purification and characterization of the AC133 antigen. The purification and characterization of the AC133 antigen, as well as the isolation of a cDNA clone is described here. Protein and nucleic acid sequence analysis of this molecule indicate that the AC133 antigen is the first described member of a new class of transmembrane receptors, having 5 transmembrane domains with little if any homology to known G-protein coupled 7 transmembrane family members.

Antibody AC133 was prepared and purified as described above and conjugated to CNBr activated sepharose. CNBr activated sepharose was purchased from Pharmacia (Alameda, Calif.), and mAb AC133 affinity resin was prepared per the manufacturer's procedure using a 25 minute ligand coupling reaction. The COS-7 and the WERI-Rb-1 retinoblastoma cell lines were obtained from American Type Culture Collection (Rockville, Md.). Custom primers were synthesized by Operon Technologies (Alameda, Calif.).

Purification of the AC133 Antigen. The AC133 antigen was isolated from 96 hour PMA activated Y79 retinoblastoma cells (commercially available, for example, from ATCC). Cells (2×10$^9$) were washed with PBS and lysed in 0.125M NaCl, 25 mM Tris pH 8, 0.005% NaN$_3$, 2.5 mM EDTA, and 2.5% Brij 99/96 (2:1) detergent containing 1.0 mM phenylmethyl sulfonylfluoride (PMSF) and a 1/1000 dilution of a 2.2 mg/ml solution of aprotinin containing 4.1 trypsin inhibitor units per mg (Sigma). Cells were vortexed intermittently for 5 minutes at room temperature and then left on ice for 20 minutes. Cell nuclei and debris were removed by centrifugation at 12,000×G for 10 minutes. Lysate supernatant was filtered through a 0.2 $\mu$M filter prior to loading onto 0.5mL mAb AC133 affinity column equilibrated in wash buffer (0.125 M NaCl, 25 mM Tris pH 8.0, 0.01% NaN$_3$, 2.5 mM EDTA, 0.1% Brij). The column was washed extensively with wash buffer and the antigen was eluted in 50 mM ethanolamine pH 11.5, 0.1% Brij, 0.01% NaN$_3$. The pH was immediately adjusted to neutral with HCl. Passage of the antigen eluate over a 300 $\mu$l bed volume DEAE column equilibrated in wash buffer removed many of contaminating proteins, and a second affinity chromatography step using an AC133 antibody column as described above resulted in >95% pure AC133 antigen amenable to proteolysis and protein sequence analysis. The purity and identity of AC133 antigen was confirmed by sodium dodecyl sulfate-polyacrylamide gel electrophoresis (SDS-PAGE) and Western analysis (Towbin, H., T. Staehelin, and J. Gordon (1979) PNAS 76,4350–4354; Towbin, H. and J. Gordon (1984) J. Immunol. Meth 72:313–340).

Endoglyconase treatment of the purified AC133 antigen. One microgram of AC133 antigen was resuspended in 50 $\mu$l water and 125 $\mu$l 0.1 M 2-mercaptoethanol and 0.5% SDS. The protein was denatured at 100° C. for 5 minutes. Denatured mixture (35 $\mu$l) was added to each of 5 tubes, together with 25 $\mu$l 0.5 M Tris pH 8, 10 $\mu$l water, 10 $\mu$l 10% NP40. 0–0.1 unit PNGase F (Sigma) was added to each tube, and the tubes were incubated at 30° C. overnight. Deglycosylated antigen was visualized on a silver stained SDS-polyacrylamide gel.

Lysyl endopeptidase digestion of the AC133 Antigen and isolation of peptides. AC133 antigen was precipitated from 1.4 mL of 2 $\mu$g/mL affinity column eluate by the addition of TCA to 10%. The precipitated dry protein was suspended in 25 $\mu$L of solution digest buffer (8M urea, 400 mM Tris pH 7.8), to which 5 $\mu$l of 45 mM DTT was added and the mixture incubated at 50° C. for 15 min. After cooling to room temperature, 5 $\mu$l of 100 mM iodoacetamide was added and the mix was incubated for an additional 15 minutes. Distilled water (70 $\mu$l) was added, diluting the urea to 2 M, and 2 pmol of the lysyl endopeptidase, LysC (commercially available from Wako Chemicals, USA), was added. The digestion was carried out at 37° C. for 24 hours. Peptides were isolated by HPLC separation on a VYDAC narrowbore C18 reverse phase column with a 4–32% acetonitrile gradient in 0.1% trifluoroacetic acid (TFA).

Protein sequence analysis of AC133 antigen peptides. N-terminal sequence analysis was determined using Edman chemistry (Edman, P., Begg, G. (1967) Eur. J. Biochem. 1, 80–91; Huwick, R. M., Hunkapillar, M. W., Hood, L. E., and Dreyer, W. J. (1987) J. Biol Chem. 256, p. 7990) on an Applied Biosystems 477A or 473A liquid pulse protein sequenator. PTH-Amino acids were separated on a Brownlee C-18 reverse phase column (2.1 mm×22 cm) at 55° C. in buffer A (3.5% tetrahydrofuran with addition of 2 to 4% ABI Premix Buffer concentrate from Applied Biosystems to buffer B (acetonitrile), with a 12–36% buffer B linear gradient over 18 min, followed by a 13 min. isocratic period at 36% B.

Isolation and protein sequencing of the AC133 antigen. The 120 kD AC133 antigen was isolated by immunoaffinity chromatography from a retinoblastoma cell line, Y79, which was PMA activated for 96 hours prior to harvest. Sequential affinity chromatography and DEAE chromatography were utilized to generate >95% pure AC133 antigen by SDS-PAGE and silver staining and the identity of the purified molecule as the AC133 antigen was confirmed by Western blotting. De-glycosylation of the antigen with PGNase F to remove N-linked sugar shows that approximately 30 kD of the molecular weight is due to glycosylation. Repeated initial attempts to sequence the N-terminus of the AC133 antigen failed, suggesting that this protein is amino-terminally blocked. However, digestion of the purified antigen with lysyl endopeptidase followed by reverse phase HPLC, yielded four peptide sequences with lengths of 12–16 amino acids. Searches of the major protein and nucleic acid databases with the peptide and resulting degenerate oligonucleotide sequences indicated that the AC133 antigen could not be identified with any described molecules. (The amino acid sequence has now been deduced from cDNA cloning and is shown in FIG. 12.)

cDNA Cloning. Total RNA was isolated from WERI-Rb-1 retinoblastoma cells (available from the American Type Culture Collection; Rockville, Md.) and poly $A^+$ RNA was prepared using the Poly $A^+$ Tract System (Promega Corp., Madison, Wis.). cDNA was synthesized (Guebler, U. and B. J. Hoffman (1983) *Gene* 25:263) using superscript reverse transcriptase (GIBCO BRL, Gaithersburg, Md.) and an oligo dT primer. The blunted cDNA was ligated to nonself-complimentary Bst XI adaptors and gel purified to remove unligated adaptors and small fragments. The Tinkered cDNA was then ligated into the pcDNA-I expression vector (Invitrogen, San Diego, Calif.) and electroporated into *Escherichia coli* strain MC1061/P3 (Dower, W. J. (1990) *Genetic Engineering* V. 12 Edited by J. K. Seflow, Plenum Press, New York 275–295. (Electroporation of Bacteria: a general approach to genetic transformation); Ausubel, F. M., R. Brent, R. E. Kingston, D. D. Moore, J. G. Seidman, J. A. Smith and K. Struhl. 1987–1994 *Current Protocols in Molecular Biology*. John Wilest Sons; N.Y.). WERI-Rb-1 library cDNA (100 ng/reaction) was used as a PCR template with 100 pmol each degenerate sense and antisense primers designed from the protein sequence of four AC133 antigen peptides. PCR reactions were carried out in buffer (50 mM KCl, 10 mM Tris pH 9, 0.1% Triton X-100, 1.5 mM MgCl, 0.2 mM (each) dNTP's) with 5 units of Taq DNA polymerase per reaction (Promega Corp, Madison, Wis.). Amplification was carried out in an MJ research (data) instrument as follows: 92° C. for 1 min, 55–37° C. for 1 min, 72° C. for 3 min, 35 cycles. After amplification the reaction mixtures were run on 1% agarose gels, and unique bands not appearing in the individual primer controls were gel purified and cloned into pCR 2.1 using a TA Cloning Kit (Invitrogen, San Diego, Calif.). The 5' and 3' ends of the gene were isolated by hemi-specific PCR with nested sets of AC133 antigen gene specific primers and library specific primers. Twenty cycles of single-stranded PCR were performed with each gene specific primer in a 50 µl reaction volume with 100 ng of the library cDNA and 10 pmol each primer in PCR reaction buffer ( described above) with 5 units of Taq polymerase. An aliquot (10 µl) of this reaction mix was removed and used as template for a second, 35 cycle, PCR reaction using both the gene specific primer and the library specific primer. An aliquot (5 µl) of this PCR reaction mix was then used for another 35 cycles of reaction using nested library and gene specific primers. Bands corresponding to the 5' and 3' ends of the gene were gel purified and cloned into pCR 2.1. Overlapping cDNA clones were sequenced by the dideoxy chain reaction using fluorescent dye terminators and an ABI sequencer (Applied Biosystems, Foster City, Calif.)

Isolation of a cDNA clone of the AC133 antigen. To isolate the cDNA for this protein, a cDNA library was prepared from the WERI-Rb-1 retinoblastoma cell line that expresses approximately 10-fold more AC133 antigen than PMA activated Y79 cells. Degenerate primers were used in low stringency PCR reactions with the library to yield a 1.7 kb fragment that contained the correct sequence of peptide 3 at the 5' end and the correct sequence of peptide 4 at the 3 prime end. Additionally, the sequence of peptide 2 was found within the fragment in the correct reading frame. Hemi-specific PCR with gene specific primers and library specific primers yielded additional 1.2 kB and 2 kB fragments corresponding to the 5' and 3' ends of the gene and overlapping with the initial 1.7 kB clone.

Sequencing of the three partial clones yielded a 4 kB cDNA containing an open reading frame of 3.0 kB, but also containing a 128 bp intron that appears to be associated with the poly $A^+$ version of the gene, and does not contain eukaryotic consensus splice sequences. To isolate an intact stem cell derived clone without the intron, AC133+ stem cells were isolated from fetal liver utilizing a magnetic conjugate of mAb AC133 and the Miltenyi magnetic separation system (Miltenyi Biotech, GMBH). Total RNA was isolated from these cells, and used as a template for RT-PCR reactions. Primers designed to span the intron generate a single 582 bp fragment with the poly A+ derived cDNA template, but generate a single 454 bp fragment without the intron from total RNA in AC133$^+$ cell lines (FIG. 3), suggesting that the spliced mRNA is the major product within the total RNA pool. RT-PCR was utilized to generate cDNA clones originating before the start methionine and containing the complete cDNA sequence. The full length cDNA encoding AC133 antigen predicts a protein of 863 amino acids with a molecular weight of 96.8 kD (FIG. 4). Hydrophobicity analysis of the sequence (FIG. 5) and transmembrane helix algorithms indicate that the protein spans the cell membrane a total of five times (FIG. 6) predicting the presence of two large (255 and 280 amino acids) extracellular loops and a C-terminal cytoplasmic tail. Other structural features suggested by the protein sequence include leucine zipper motifs in both of the putative large extracellular loops and six consensus sequences for N-glycosylation.

Expression of the AC133 antigen in transfected COS-7 cells. AC133 positive cells ($1 \times 10^7$) were isolated from fetal liver as described above. Total RNA was isolated using RNAzol (Gibco BRL, Gaithersburg, Md.) as described (Chomczynski, P. and Sacchi, N. (1987) *Anal. Biochem.* 162, 156). RT-PCR was performed using the Promega Access RT-PCR system (Promega Corp, Madison, Wis.) with 10 ng total RNA template and primers directed before the start methionine and after the stop codon. The 2.8 kb band corresponding to the coding region of the gene was cloned into the Invitrogen directional eukaryotic TA cloning vector (pCR 3.1) containing the CMV promoter. Subconfluent COS-7 cells (available from the ATCC, Rockville, Md.) were transfected with 5 μg of cloned DNA by electroporation and incubated for 48 hours prior to FACS analysis. Transfected COS-7 cells were stained with 50 ng/100 μl test mAb AC133-PE, and analyzed with a Becton Dickenson (San Jose, Calif.) FACS scan.

Figure 7A:
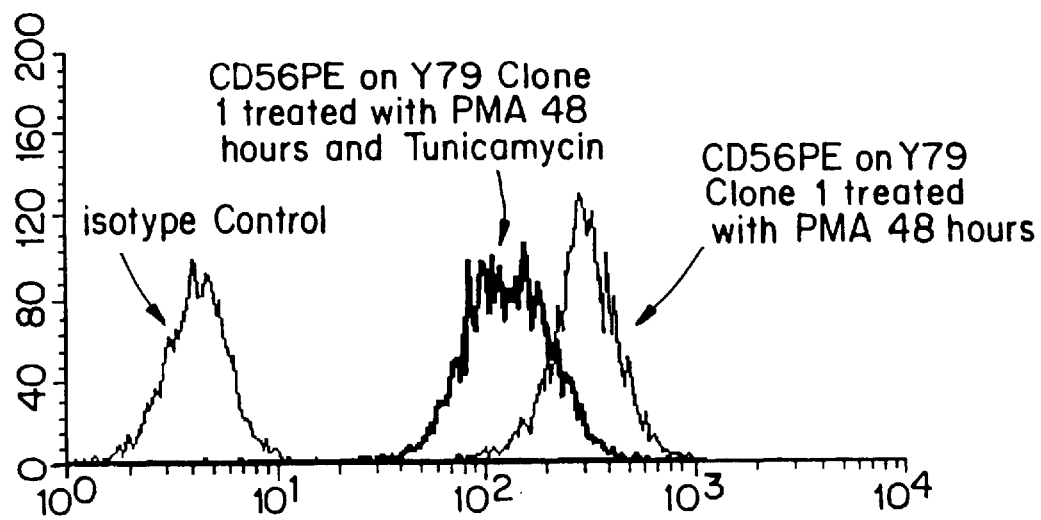
FIGS. 7A and 7B are graphs showing FACS analysis of CD56 (FIG. 7A) and AC133 antigen (FIG. 7B) expression on PMA activated, tunicamycin treated or untreated Y79.1 cells.
Figure 7B:
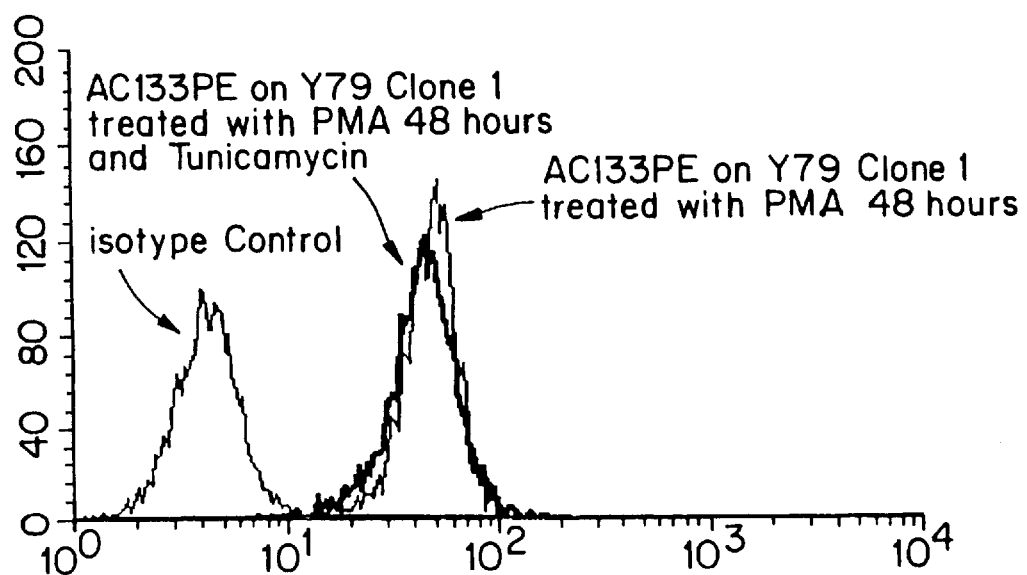

Expression of the AC133 antigen in COS cells. COS cells transfected with the AC133 antigen gene were stained with mAb AC133-PE and analyzed by FACS (FIG. 7). Cos cells transfected with the AC133 antigen gene stain brightly with mAB AC133-PE, however, untransfected cells, cells transfected with empty vector or the gene for CD-8 do not stain with this antibody.

AC133 expression in various lymphoid and non-lymphoid cell lines. The presence of AC133 antigen transcript in a variety of cell lines was assessed by Northern analysis. Northern blot analysis was performed by using Clontech (Palo Alto, Calif.) multiple tissue northern blots, and by resolving RNA samples on a 1% agarose-2M formaldehyde gel and capillary blotting overnight into nylon membrane. Total RNA was isolated with Tri Reagent, and 15 μg was loaded per lane. Staining of the blot with methylene blue was used to monitor RNA concentrations. An 800 bp EcoRI fragment of the cDNA was labelled with 32P-dCTP by random priming and used as a probe.

The presence of AC133 antigen transcript in a variety of cell lines was assessed by Northern analysis. A 4.4 kB mRNA transcript was detectable in WERI-Rb-1 cells as well as Y79 cells and MACS-isolated AC133+ fetal liver cells. While expression of the AC133 antigen is enhanced in Y79 cells upon PMA activation, the corresponding mRNA appears to be downregulated. In normal hemtopoetic tissue, the AC133 antigen message is detectable in fetal liver, and weakly detectable in adult bone marrow as expected due to the fact that AC133+ cells in these tissues are in a minority. The AC133 antigen transcript was also noted in non-lymphoid tissues, particularly in pancreas, kidney, and placenta. Weaker signals were observed for liver, lung, brain, and heart. This is in contrast to immunohistochemical staining of paraffin tissue sections were AC133 antigen expression was detectable only in bone marrow.

In a similar manner, other antibodies have been developed that are specific for the AC133 antigen. The following table shows antibodies, immunogens, isotypes, and cross blocking for a panel of such antibodies.

| Antibody | Immunogen | Isotype | AC133 cross blocking |
|----------|-----------|---------|----------------------|
| AC133 | HSC | IgG1 kappa | +++ |
| AC139 | WERI-Rb-1 | IgG1 kappa | +++ |
| AC140 | WERI-Rb-1 | IgG1 kappa | +/− |
| AC141 | WERI-Rb-1 | IgG1 kappa | − |
| AC142 | WERI-Rb-1 | IgG1 kappa | ND |

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications can be made thereto without departing from the spirit or scope of the appended claims.

What is claimed is:

1. An isolated polypeptide, wherein said polypeptide comprises the amino acid sequence of AC133 as set forth in SEQ ID NO: 2.

2. An isolated polypeptide, wherein said polypeptide comprises an amino acid sequence wherein said sequence comprises a subsequence of at least 10 amino acids in length of the amino acid sequence of AC133 as set forth in SEQ ID NO: 2, and wherein said subsequence comprises an epitope of AC133.

3. A polypeptide complex consisting of the polypeptide of claim 1 complexed to a ligand.

4. The polypeptide complex of claim 3, wherein said ligand is an antibody.

5. An isolated polypeptide, wherein said polypeptide comprises the amino acid sequence from extracellular N-terminus, aa 20–107; first transmembrane region, aa 107–126; first cytoplasmic loop, aa 127–157; second transmembrane region, aa 158–179; first extracellular loop, aa 180–435; third transmembrane region, aa 436–454; second cytoplasmic loop, aa 455–480; fourth transmembrane region, aa 481–503; second extracellular loop, aa 504–792; fifth transmembrane, aa 793–816; or cytoplasmic C-terminus, aa 817–865; of SEQ ID NO:2, wherein said polypeptide comprises an epitope of AC133.

6. The polypeptide of claim 1, wherein said polypeptide is not glycosylated.

7. The polypeptide of claim 1, wherein said polypeptide is glycosylated.

8. The polypeptide of claim 2, wherein said polypeptide is not glycosylated.

9. The polypeptide of claim 2, wherein said potypeptide is glycosylated.

* * * * *

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
      (A) LENGTH: 3804 base pairs
      (B) TYPE: nucleic acid
      (C) STRANDEDNESS: double
      (D) TOPOLOGY: linear (ii) MOLECULE TYPE: cDNA (iii) HYPOTHETICAL: NO (ix) FEATURE:
      (A) NAME/KEY: CDS
      (B) LOCATION: 38..2633

(xi) SEQUENCE DESCRIPTION: SEQ ID NO:1:

```
CCAAGTTCTA CCTCATGTTT GGAGGATCTT GCTAGCT ATG GCC CTC GTA CTC GGC        55
                                        Met Ala Leu Val Leu Gly
                                         1               5

TCC CTG TTG CTG CTG GGG CTG TGC GGG AAC TCC TTT TCA GGA GGG CAG        103
Ser Leu Leu Leu Leu Gly Leu Cys Gly Asn Ser Phe Ser Gly Gly Gln
         10                  15                  20

CCT TCA TCC ACA GAT GCT CCT AAG GCT TGG AAT TAT GAA TTG CCT GCA        151
```

```
Pro Ser Ser Thr Asp Ala Pro Lys Ala Trp Asn Tyr Glu Leu Pro Ala
        25                  30                  35

ACA AAT TAT GAG ACC CAA GAC TCC CAT AAA GCT GGA CCC ATT GGC ATT      199
Thr Asn Tyr Glu Thr Gln Asp Ser His Lys Ala Gly Pro Ile Gly Ile
        40                  45                  50

CTC TTT GAA CTA GTG CAT ATC TTT CTC TAT GTG GTA CAG CCG CGT GAT      247
Leu Phe Glu Leu Val His Ile Phe Leu Tyr Val Val Gln Pro Arg Asp
55                  60                  65                  70

TTC CCA GAA GAT ACT TTG AGA AAA TTC TTA CAG AAG GCA TAT GAA TCC      295
Phe Pro Glu Asp Thr Leu Arg Lys Phe Leu Gln Lys Ala Tyr Glu Ser
                75                  80                  85

AAA ATT GAT TAT GAC AAG CCA GAA ACT GTA ATC TTA GGT CTA AAG ATT      343
Lys Ile Asp Tyr Asp Lys Pro Glu Thr Val Ile Leu Gly Leu Lys Ile
            90                  95                 100

GTC TAC TAT GAA GCA GGG ATT ATT CTA TGC TGT GTC CTG GGG CTG CTG      391
Val Tyr Tyr Glu Ala Gly Ile Ile Leu Cys Cys Val Leu Gly Leu Leu
                105                 110                 115

TTT ATT ATT CTG ATG CCT CTG GTG GGG TAT TTC TTT TGT ATG TGT CGT      439
Phe Ile Ile Leu Met Pro Leu Val Gly Tyr Phe Phe Cys Met Cys Arg
        120                 125                 130

TGC TGT AAC AAA TGT GGT GGA GAA ATG CAC CAG CGA CAG AAG GAA AAT      487
Cys Cys Asn Lys Cys Gly Gly Glu Met His Gln Arg Gln Lys Glu Asn
135                 140                 145                 150

GGG CCC TTC CTG AGG AAA TGC TTT GCA ATC TCC CTG TTG GTG ATT TGT      535
Gly Pro Phe Leu Arg Lys Cys Phe Ala Ile Ser Leu Leu Val Ile Cys
                155                 160                 165

ATA ATA ATA AGC ATT GGC ATC TTC TAT GGT TTT GTG GCA AAT CAC CAG      583
Ile Ile Ile Ser Ile Gly Ile Phe Tyr Gly Phe Val Ala Asn His Gln
            170                 175                 180

GTA AGA ACC CGG ATC AAA AGG AGT CGG AAA CTG GCA GAT AGC AAT TTC      631
Val Arg Thr Arg Ile Lys Arg Ser Arg Lys Leu Ala Asp Ser Asn Phe
                185                 190                 195

AAG GAC TTG CGA ACT CTC TTG AAT GAA ACT CCA GAG CAA ATC AAA TAT      679
Lys Asp Leu Arg Thr Leu Leu Asn Glu Thr Pro Glu Gln Ile Lys Tyr
200                 205                 210

ATA TTG GCC CAG TAC AAC ACT ACC AAG GAC AAG GCG TTC ACA GAT CTG      727
Ile Leu Ala Gln Tyr Asn Thr Thr Lys Asp Lys Ala Phe Thr Asp Leu
215                 220                 225                 230

AAC AGT ATC AAT TCA GTG CTA GGA GGC GGA ATT CTT GAC CGA CTG AGA      775
Asn Ser Ile Asn Ser Val Leu Gly Gly Gly Ile Leu Asp Arg Leu Arg
                235                 240                 245

CCC AAC ATC ATC CCT GTT CTT GAT GAG ATT AAG TCC ATG GCA ACA GCG      823
Pro Asn Ile Ile Pro Val Leu Asp Glu Ile Lys Ser Met Ala Thr Ala
            250                 255                 260

ATC AAG GAG ACC AAA GAG GCG TTG GAG AAC ATG AAC AGC ACC TTG AAG      871
Ile Lys Glu Thr Lys Glu Ala Leu Glu Asn Met Asn Ser Thr Leu Lys
                265                 270                 275

AGC TTG CAC CAA CAA AGT ACA CAG CTT AGC AGC AGT CTG ACC AGC GTG      919
Ser Leu His Gln Gln Ser Thr Gln Leu Ser Ser Ser Leu Thr Ser Val
280                 285                 290

AAA ACT AGC CTG CGG TCA TCT CTC AAT GAC CCT CTG TGC TTG GTG CAT      967
Lys Thr Ser Leu Arg Ser Ser Leu Asn Asp Pro Leu Cys Leu Val His
295                 300                 305                 310

CCA TCA AGT GAA ACC TGC AAC AGC ATC AGA TTG TCT CTA AGC CAG CTG     1015
Pro Ser Ser Glu Thr Cys Asn Ser Ile Arg Leu Ser Leu Ser Gln Leu
                315                 320                 325

AAT AGC AAC CCT GAA CTG AGG CAG CTT CCA CCC GTG GAT GCA GAA CTT     1063
Asn Ser Asn Pro Glu Leu Arg Gln Leu Pro Pro Val Asp Ala Glu Leu
            330                 335                 340
```

```
GAC AAC GTT AAT AAC GTT CTT AGG ACA GAT TTG GAT GGC CTG GTC CAA      1111
Asp Asn Val Asn Asn Val Leu Arg Thr Asp Leu Asp Gly Leu Val Gln
        345                 350                 355

CAG GGC TAT CAA TCC CTT AAT GAT ATA CCT GAC AGA GTA CAA CGC CAA      1159
Gln Gly Tyr Gln Ser Leu Asn Asp Ile Pro Asp Arg Val Gln Arg Gln
360                 365                 370

ACC ACG ACT GTC GTA GCA GGT ATC AAA AGG GTC TTG AAT TCC ATT GGT      1207
Thr Thr Thr Val Val Ala Gly Ile Lys Arg Val Leu Asn Ser Ile Gly
375                 380                 385                 390

TCA GAT ATC GAC AAT GTA ACT CAG CGT CTT CCT ATT CAG GAT ATA CTC      1255
Ser Asp Ile Asp Asn Val Thr Gln Arg Leu Pro Ile Gln Asp Ile Leu
            395                 400                 405

TCA GCA TTC TCT GTT TAT GTT AAT AAC ACT GAA AGT TAC ATC CAC AGA      1303
Ser Ala Phe Ser Val Tyr Val Asn Asn Thr Glu Ser Tyr Ile His Arg
                410                 415                 420

AAT TTA CCT ACA TTG GAA GAG TAT GAT TCA TAC TGG TGG CTG GGT GGC      1351
Asn Leu Pro Thr Leu Glu Glu Tyr Asp Ser Tyr Trp Trp Leu Gly Gly
            425                 430                 435

CTG GTC ATC TGC TCT CTG CTG ACC CTC ATC GTG ATT TTT TAC TAC CTG      1399
Leu Val Ile Cys Ser Leu Leu Thr Leu Ile Val Ile Phe Tyr Tyr Leu
        440                 445                 450

GGC TTA CTG TGT GGC GTG TGC GGC TAT GAC AGG CAT GCC ACC CCG ACC      1447
Gly Leu Leu Cys Gly Val Cys Gly Tyr Asp Arg His Ala Thr Pro Thr
455                 460                 465                 470

ACC CGA GGC TGT GTC TCC AAC ACC GGA GGC GTC TTC CTC ATG GTT GGA      1495
Thr Arg Gly Cys Val Ser Asn Thr Gly Gly Val Phe Leu Met Val Gly
                475                 480                 485

GTT GGA TTA AGT TTC CTC TTT TGC TGG ATA TTG ATG ATC ATT GTG GTT      1543
Val Gly Leu Ser Phe Leu Phe Cys Trp Ile Leu Met Ile Ile Val Val
            490                 495                 500

CTT ACC TTT GTC TTT GGT GCA AAT GTG GAA AAA CTG ATC TGT GAA CCT      1591
Leu Thr Phe Val Phe Gly Ala Asn Val Glu Lys Leu Ile Cys Glu Pro
        505                 510                 515

TAC ACG AGC AAG GAA TTA TTC CGG GTT TTG GAT ACA CCC TAC TTA CTA      1639
Tyr Thr Ser Lys Glu Leu Phe Arg Val Leu Asp Thr Pro Tyr Leu Leu
520                 525                 530

AAT GAA GAC TGG GAA TAC TAT CTC TCT GGG AAG CTA TTT AAT AAA TCA      1687
Asn Glu Asp Trp Glu Tyr Tyr Leu Ser Gly Lys Leu Phe Asn Lys Ser
535                 540                 545                 550

AAA ATG AAG CTC ACT TTT GAA CAA GTT TAC AGT GAC TGC AAA AAA AAT      1735
Lys Met Lys Leu Thr Phe Glu Gln Val Tyr Ser Asp Cys Lys Lys Asn
                555                 560                 565

AGA GGC ACT TAC GGC ACT CTT CAC CTG CAG AAC AGC TTC AAT ATC AGT      1783
Arg Gly Thr Tyr Gly Thr Leu His Leu Gln Asn Ser Phe Asn Ile Ser
            570                 575                 580

GAA CAT CTC AAC ATT AAT GAG CAT ACT GGA AGC ATA AGC AGT GAA TTG      1831
Glu His Leu Asn Ile Asn Glu His Thr Gly Ser Ile Ser Ser Glu Leu
        585                 590                 595

GAA AGT CTG AAG GTA AAT CTT AAT ATC TTT CTG TTG GGT GCA GCA GGA      1879
Glu Ser Leu Lys Val Asn Leu Asn Ile Phe Leu Leu Gly Ala Ala Gly
600                 605                 610

AGA AAA AAC CTT CAG GAT TTT GCT GCT TGT GGA ATA GAC AGA ATG AAT      1927
Arg Lys Asn Leu Gln Asp Phe Ala Ala Cys Gly Ile Asp Arg Met Asn
615                 620                 625                 630

TAT GAC AGC TAC TTG GCT CAG ACT GGT AAA TCC CCC GCA GGA GTG AAT      1975
Tyr Asp Ser Tyr Leu Ala Gln Thr Gly Lys Ser Pro Ala Gly Val Asn
                635                 640                 645

CTT TTA TCA TTT GCA TAT GAT CTA GAA GCA AAA GCA AAC AGT TTG CCC      2023
Leu Leu Ser Phe Ala Tyr Asp Leu Glu Ala Lys Ala Asn Ser Leu Pro
            650                 655                 660
```

```
CCA GGA AAT TTG AGG AAC TCC CTG AAA AGA GAT GCA CAA ACT ATT AAA    2071
Pro Gly Asn Leu Arg Asn Ser Leu Lys Arg Asp Ala Gln Thr Ile Lys
            665                 670                 675

ACA ATT CAC CAG CAA CGA GTC CTT CCT ATA GAA CAA TCA CTG AGC ACT    2119
Thr Ile His Gln Gln Arg Val Leu Pro Ile Glu Gln Ser Leu Ser Thr
            680                 685                 690

CTA TAC CAA AGC GTC AAG ATA CTT CAA CGC ACA GGG AAT GGA TTG TTG    2167
Leu Tyr Gln Ser Val Lys Ile Leu Gln Arg Thr Gly Asn Gly Leu Leu
695                 700                 705                 710

GAG AGA GTA ACT AGG ATT CTA GCT TCT CTG GAT TTT GCT CAG AAC TTC    2215
Glu Arg Val Thr Arg Ile Leu Ala Ser Leu Asp Phe Ala Gln Asn Phe
            715                 720                 725

ATC ACA AAC AAT ACT TCC TCT GTT ATT ATT GAG GAA ACT AAG AAG TAT    2263
Ile Thr Asn Asn Thr Ser Ser Val Ile Ile Glu Glu Thr Lys Lys Tyr
            730                 735                 740

GGG AGA ACA ATA ATA GGA TAT TTT GAA CAT TAT CTG CAG TGG ATC GAG    2311
Gly Arg Thr Ile Ile Gly Tyr Phe Glu His Tyr Leu Gln Trp Ile Glu
            745                 750                 755

TTC TCT ATC AGT GAG AAA GTG GCA TCG TGC AAA CCT GTG GCC ACC GCT    2359
Phe Ser Ile Ser Glu Lys Val Ala Ser Cys Lys Pro Val Ala Thr Ala
            760                 765                 770

CTA GAT ACT GCT GTT GAT GTC TTT CTG TGT AGC TAC ATT ATC GAC CCC    2407
Leu Asp Thr Ala Val Asp Val Phe Leu Cys Ser Tyr Ile Ile Asp Pro
775                 780                 785                 790

TTG AAT TTG TTT TGG TTT GGC ATA GGA AAA GCT ACT GTA TTT TTA CTT    2455
Leu Asn Leu Phe Trp Phe Gly Ile Gly Lys Ala Thr Val Phe Leu Leu
            795                 800                 805

CCG GCT CTA ATT TTT GCG GTA AAA CTG GCT AAG TAC TAT CGT CGA ATG    2503
Pro Ala Leu Ile Phe Ala Val Lys Leu Ala Lys Tyr Tyr Arg Arg Met
            810                 815                 820

GAT TCG GAG GAC GTG TAC GAT GAT GTT GAA ACT ATA CCC ATG AAA AAT    2551
Asp Ser Glu Asp Val Tyr Asp Asp Val Glu Thr Ile Pro Met Lys Asn
            825                 830                 835

ATG GAA AAT GGT AAT AAT GGT TAT CAT AAA GAT CAT GTA TAT GGT ATT    2599
Met Glu Asn Gly Asn Asn Gly Tyr His Lys Asp His Val Tyr Gly Ile
            840                 845                 850

CAC AAT CCT GTT ATG ACA AGC CCA TCA CAA CAT T GATAGCTGAT           2643
His Asn Pro Val Met Thr Ser Pro Ser Gln His
855                 860                 865

GTTGAAACTG CTTGAGCATC AGGATACTCA AAGTGGAAAG GATCACAGAT TTTTGGTAGT    2703
TTCTGGGTCT ACAAGGACTT TCCAAATCCA GGAGCAACGC CAGTGGCAAC GTAGTGACTC    2763
AGGCGGGCAC CAAGGCAACG GCACCATTGG TCTCTGGGTA GTGCTTTAAG AATGAACACA    2823
ATCACGTTAT AGTCCATGGT CCATCACTAT TCAAGGATGA CTCCCTCCCT TCCTGTCTAT    2883
TTTTGTTTTT TACTTTTTTA CACTGAGTTT CTATTTAGAC ACTACAACAT ATGGGGTGTT    2943
TGTTCCCATT GGATGCATTT CTATCAAAAC TCTATCAAAT GTGATGGCTA GATTCTAACA    3003
TATTGCCATG TGTGGAGTGT GCTGAACACA CACCAGTTTA CAGGAAAGAT GCATTTGTG    3063
TACAGTAAAC GGTGTATATA CCTTTTGTTA CCACAGAGTT TTTAAACAA ATGAGTATTA    3123
TAGGACTTTC TTCTAAATGA GCTAAATAAG TCACCATTGA CTTCTTGGTG CTGTTGAAAA    3183
TAATCCATTT TCACTAAAAG TGTGTGAAAC CTACAGCATA TTCTTCACGC AGAGATTTTC    3243
ATCTATTATA CTTTATCAAA GATTGGCCAT GTTCCACTTG GAAATGGCAT GCAAAAGCCA    3303
TCATAGAGAA ACCTGCGTAA CTCCATCTGA CAAATTCAAA AGAGAGAGAG AGATCTTGAG    3363
AGAGAAATGC TGTTCGTTCA AAAGTGGAGT TGTTTTAACA GATGCCAATT ACGGTGTACA    3423
```

```
GTTTAACAGA GTTTTCTGTT GCATTAGGAT AAACATTAAT TGGAGTGCAG CTAACATGAG    3483

TATCATCAGA CTAGTATCAA GTGTTCTAAA ATGAAATATG AGAAGATCCT GTCACAATTC    3543

TTAGATCTGG TGTCCAGCAT GGATGAAACC TTTGAGTTTG GTCCCTAAAT TTGCATGAAA    3603

GCACAAGGTA AATATTCATT TGCTTCAGGA GTTTCATGTT GGATCTGTCA TTATCAAAAG    3663

TGATCAGCAA TGAAGAACTG GTCGGACAAA ATTTAACGTT GATGTAATGG AATTCCAGAT    3723

GTAGGCATTC CCCCCAGGTC TTTTCATGTG CAGATTGCAG TTCTGATTCA TTTGAATAAA    3783

AAGGAACTTG GAAAAAAAAA A                                              3804

(2) INFORMATION FOR SEQ ID NO:2:

(i) SEQUENCE CHARACTERISTICS:
        (A) LENGTH: 865 amino acids
        (B) TYPE: amino acid
        (D) TOPOLOGY: linear (ii) MOLECULE TYPE: protein (xi) SEQUENCE DESCRIPTION: SEQ ID NO:2:

Met Ala Leu Val Leu Gly Ser Leu Leu Leu Gly Leu Cys Gly Asn
 1               5                  10                  15

Ser Phe Ser Gly Gly Gln Pro Ser Ser Thr Asp Ala Pro Lys Ala Trp
                20                  25                  30

Asn Tyr Glu Leu Pro Ala Thr Asn Tyr Glu Thr Gln Asp Ser His Lys
            35                  40                  45

Ala Gly Pro Ile Gly Ile Leu Phe Glu Leu Val His Ile Phe Leu Tyr
        50                  55                  60

Val Val Gln Pro Arg Asp Phe Pro Glu Asp Thr Leu Arg Lys Phe Leu
65                  70                  75                  80

Gln Lys Ala Tyr Glu Ser Lys Ile Asp Tyr Asp Lys Pro Glu Thr Val
                85                  90                  95

Ile Leu Gly Leu Lys Ile Val Tyr Tyr Glu Ala Gly Ile Ile Leu Cys
            100                 105                 110

Cys Val Leu Gly Leu Leu Phe Ile Ile Leu Met Pro Leu Val Gly Tyr
        115                 120                 125

Phe Phe Cys Met Cys Arg Cys Cys Asn Lys Cys Gly Gly Glu Met His
    130                 135                 140

Gln Arg Gln Lys Glu Asn Gly Pro Phe Leu Arg Lys Cys Phe Ala Ile
145                 150                 155                 160

Ser Leu Leu Val Ile Cys Ile Ile Ile Ser Ile Gly Ile Phe Tyr Gly
                165                 170                 175

Phe Val Ala Asn His Gln Val Arg Thr Arg Ile Lys Arg Ser Arg Lys
            180                 185                 190

Leu Ala Asp Ser Asn Phe Lys Asp Leu Arg Thr Leu Leu Asn Glu Thr
        195                 200                 205

Pro Glu Gln Ile Lys Tyr Ile Leu Ala Gln Tyr Asn Thr Thr Lys Asp
    210                 215                 220

Lys Ala Phe Thr Asp Leu Asn Ser Ile Asn Ser Val Leu Gly Gly Gly
225                 230                 235                 240

Ile Leu Asp Arg Leu Arg Pro Asn Ile Ile Pro Val Leu Asp Glu Ile
                245                 250                 255

Lys Ser Met Ala Thr Ala Ile Lys Glu Thr Lys Glu Ala Leu Glu Asn
            260                 265                 270

Met Asn Ser Thr Leu Lys Ser Leu His Gln Gln Ser Thr Gln Leu Ser
        275                 280                 285
```

-continued

```
Ser Ser Leu Thr Ser Val Lys Thr Ser Leu Arg Ser Ser Leu Asn Asp
    290                 295                 300

Pro Leu Cys Leu Val His Pro Ser Ser Glu Thr Cys Asn Ser Ile Arg
305                 310                 315                 320

Leu Ser Leu Ser Gln Leu Asn Ser Asn Pro Glu Leu Arg Gln Leu Pro
                325                 330                 335

Pro Val Asp Ala Glu Leu Asp Asn Val Asn Asn Val Leu Arg Thr Asp
                340                 345                 350

Leu Asp Gly Leu Val Gln Gln Gly Tyr Gln Ser Leu Asn Asp Ile Pro
            355                 360                 365

Asp Arg Val Gln Arg Gln Thr Thr Thr Val Val Ala Gly Ile Lys Arg
    370                 375                 380

Val Leu Asn Ser Ile Gly Ser Asp Ile Asp Asn Val Thr Gln Arg Leu
385                 390                 395                 400

Pro Ile Gln Asp Ile Leu Ser Ala Phe Ser Val Tyr Val Asn Asn Thr
                405                 410                 415

Glu Ser Tyr Ile His Arg Asn Leu Pro Thr Leu Glu Glu Tyr Asp Ser
                420                 425                 430

Tyr Trp Trp Leu Gly Gly Leu Val Ile Cys Ser Leu Leu Thr Leu Ile
            435                 440                 445

Val Ile Phe Tyr Tyr Leu Gly Leu Leu Cys Gly Val Cys Gly Tyr Asp
    450                 455                 460

Arg His Ala Thr Pro Thr Thr Arg Gly Cys Val Ser Asn Thr Gly Gly
465                 470                 475                 480

Val Phe Leu Met Val Gly Val Gly Leu Ser Phe Leu Phe Cys Trp Ile
                485                 490                 495

Leu Met Ile Ile Val Val Leu Thr Phe Val Phe Gly Ala Asn Val Glu
                500                 505                 510

Lys Leu Ile Cys Glu Pro Tyr Thr Ser Lys Glu Leu Phe Arg Val Leu
            515                 520                 525

Asp Thr Pro Tyr Leu Leu Asn Glu Asp Trp Glu Tyr Tyr Leu Ser Gly
    530                 535                 540

Lys Leu Phe Asn Lys Ser Lys Met Lys Leu Thr Phe Glu Gln Val Tyr
545                 550                 555                 560

Ser Asp Cys Lys Lys Asn Arg Gly Thr Tyr Gly Thr Leu His Leu Gln
                565                 570                 575

Asn Ser Phe Asn Ile Ser Glu His Leu Asn Ile Asn Glu His Thr Gly
                580                 585                 590

Ser Ile Ser Ser Glu Leu Glu Ser Leu Lys Val Asn Leu Asn Ile Phe
            595                 600                 605

Leu Leu Gly Ala Ala Gly Arg Lys Asn Leu Gln Asp Phe Ala Ala Cys
    610                 615                 620

Gly Ile Asp Arg Met Asn Tyr Asp Ser Tyr Leu Ala Gln Thr Gly Lys
625                 630                 635                 640

Ser Pro Ala Gly Val Asn Leu Leu Ser Phe Ala Tyr Asp Leu Glu Ala
                645                 650                 655

Lys Ala Asn Ser Leu Pro Pro Gly Asn Leu Arg Asn Ser Leu Lys Arg
                660                 665                 670

Asp Ala Gln Thr Ile Lys Thr Ile His Gln Gln Arg Val Leu Pro Ile
            675                 680                 685

Glu Gln Ser Leu Ser Thr Leu Tyr Gln Ser Val Lys Ile Leu Gln Arg
    690                 695                 700
```

-continued

```
Thr Gly Asn Gly Leu Leu Glu Arg Val Thr Arg Ile Leu Ala Ser Leu
705                 710                 715                 720

Asp Phe Ala Gln Asn Phe Ile Thr Asn Asn Thr Ser Ser Val Ile Ile
            725                 730                 735

Glu Glu Thr Lys Lys Tyr Gly Arg Thr Ile Ile Gly Tyr Phe Glu His
            740                 745                 750

Tyr Leu Gln Trp Ile Glu Phe Ser Ile Ser Glu Lys Val Ala Ser Cys
        755                 760                 765

Lys Pro Val Ala Thr Ala Leu Asp Thr Ala Val Asp Val Phe Leu Cys
        770                 775                 780

Ser Tyr Ile Ile Asp Pro Leu Asn Leu Phe Trp Phe Gly Ile Gly Lys
785                 790                 795                 800

Ala Thr Val Phe Leu Leu Pro Ala Leu Ile Phe Ala Val Lys Leu Ala
            805                 810                 815

Lys Tyr Tyr Arg Arg Met Asp Ser Glu Asp Val Tyr Asp Asp Val Glu
                820                 825                 830

Thr Ile Pro Met Lys Asn Met Glu Asn Gly Asn Asn Gly Tyr His Lys
            835                 840                 845

Asp His Val Tyr Gly Ile His Asn Pro Val Met Thr Ser Pro Ser Gln
    850                 855                 860

His
865
```